US012224062B2

(12) United States Patent
Besanson et al.

(10) Patent No.: US 12,224,062 B2
(45) Date of Patent: Feb. 11, 2025

(54) UTILIZING NEURAL NETWORK MODELS FOR RECOMMENDING AND ADAPTING TREATMENTS FOR USERS

(71) Applicant: Accenture Global Solutions Limited, Dublin (IE)

(72) Inventors: Gaston Besanson, Barcelona (ES); Frode Huse Gjendem, Barcelona (ES); Bernabé Marcos Montes, Barcelona (ES); Joan Verdu Arnal, Taragona (ES)

(73) Assignee: Accenture Global Solutions Limited, Dublin (IE)

( * ) Notice: Subject to any disclaimer, the term of this patent is extended or adjusted under 35 U.S.C. 154(b) by 1048 days.

(21) Appl. No.: 17/164,433

(22) Filed: Feb. 1, 2021

(65) Prior Publication Data

US 2022/0172838 A1 Jun. 2, 2022

(30) Foreign Application Priority Data

Nov. 30, 2020 (EP) .................... 20383037

(51) Int. Cl.
*G16H 50/20* (2018.01)
*A61B 5/00* (2006.01)
(Continued)

(52) U.S. Cl.
CPC .......... *G16H 50/20* (2018.01); *A61B 5/4836* (2013.01); *A61B 5/7267* (2013.01); *G06N 3/045* (2023.01);
(Continued)

(58) Field of Classification Search
CPC ............... A61B 5/4836; A61B 5/7267; G06N 20/10; G06N 3/045; G06N 3/0454; G06N 3/08;
(Continued)

(56) References Cited

U.S. PATENT DOCUMENTS

2014/0279746 A1* 9/2014 De Bruin ............... G16H 50/70
706/46
2019/0267121 A1* 8/2019 de Sousa Moura ... G16H 50/20
(Continued)

FOREIGN PATENT DOCUMENTS

WO WO-2019174898 A1 * 9/2019 ............. G16H 50/20

OTHER PUBLICATIONS

Zarei, Anahita, et al. "An intelligent system for prediction of orthodontic treatment outcome." The 2006 IEEE International Joint Conference on Neural Network Proceedings. IEEE, 2006. (Year: 2006).*

(Continued)

*Primary Examiner* — Randall K. Baldwin
(74) *Attorney, Agent, or Firm* — Polsinelli PC

(57) ABSTRACT

A device may receive user data identifying vitals of users when receiving treatments and dosages of the treatments, and may process the user data, with a divergence model, to determine divergence data identifying divergences between the users. The device may process the divergence data, with a clustering model, to group the users into clusters of users, and may train a first neural network model, with the user data, to generate a trained first neural network model. The device may train a second neural network model, with the user data, to generate a trained second neural network model, and may generate a treatment model based on the trained first and second neural network models. The device may process new user data identifying a new user, with the treatment model, to determine a recommended treatment for the new user, and may perform one or more actions based on the recommended treatment.

18 Claims, 10 Drawing Sheets

(51) Int. Cl.
| | |
|---|---|
| *G06N 3/045* | (2023.01) |
| *G06N 3/08* | (2023.01) |
| *G16H 10/60* | (2018.01) |
| *G16H 20/10* | (2018.01) |
| *G16H 50/30* | (2018.01) |
| *G16H 50/70* | (2018.01) |

(52) U.S. Cl.
CPC ............... *G06N 3/08* (2013.01); *G16H 10/60* (2018.01); *G16H 20/10* (2018.01); *G16H 50/30* (2018.01); *G16H 50/70* (2018.01)

(58) Field of Classification Search
CPC ........ G16H 10/60; G16H 20/10; G16H 50/20; G16H 50/30; G16H 50/70
See application file for complete search history.

(56) References Cited

U.S. PATENT DOCUMENTS

| | | | | |
|---|---|---|---|---|
| 2020/0118458 | A1* | 4/2020 | Shriberg | G16H 40/67 |
| 2020/0143922 | A1* | 5/2020 | Chekroud | G16H 20/10 |
| 2021/0117842 | A1* | 4/2021 | Smith | G06N 3/088 |
| 2021/0202088 | A1* | 7/2021 | Neumann | G16H 20/00 |
| 2021/0232934 | A1* | 7/2021 | Lai | G06N 20/00 |
| 2021/0265064 | A1* | 8/2021 | Hendriks | G16H 40/67 |
| 2022/0344049 | A1* | 10/2022 | Hall | G06N 3/0464 |

OTHER PUBLICATIONS

Sinha, Yash Pratyush, et al. "Contextual care protocol using neural networks and decision trees." 2018 Second International Conference on Advances in Electronics, Computers and Communications (ICAECC). IEEE, 2018. (Year: 2018).*
Allam, Ahmed, et al. "Patient similarity analysis with longitudinal health data." arXiv preprint arXiv:2005.06630 (May 2020). (Year: 2020).*
Hatwell, Julian, Mohamed Medhat Gaber, and R. Muhammad Atif Azad. "Ada-WHIPS: explaining AdaBoost classification with applications in the health sciences." (Oct. 2020). (Year: 2020).*
Doctor, Faiyaz, Raouf NG Naguib, and Rahat Iqbal. "A Neuro-Fuzzy Approach for Identifying Practice Variations Based on Modelling Relationships between Clinical Variables and Treatment Decisions." 2011 Developments in E-systems Engineering. IEEE, 2011. (Year: 2011).*
Johnson, Alistair EW, et al. "Machine learning and decision support in critical care." Proceedings of the IEEE 104.2 (2016): 444-466. (Year: 2016).*
Singh, Chandan, W. James Murdoch, and Bin Yu. "Hierarchical interpretations for neural network predictions." arXiv preprint arXiv: 1806.05337 v2 (2019). (Year: 2019).*
Dalla Man et al., "The UVA/PADOVA Type 1 Diabetes Simulator: New Features," Journal of Diabetes Science and Technology, 2014, vol. 8(1), pp. 26-34 [retrieved from https://www.ncbi.nlm.nih.gov/pmc/articles/PMC4454102].
Clarke et al., "Statistical Tools to Analyze Continuous Glucose Monitor Data," Diabetes Technology & Therapeutics, 2009, vol. 11, Supplement 1, pp. 45-54 [retrieved from https://www.ncbi.nlm.nih.gov/pmc/articles/PMC2903980/pdf/dia.2008.0138.pdf].
Xie, simglucose, (2021), GitHub repository [retrieved from https://github.com/jxx123/simglucose].
De Paula, et al., "On-line policy learning and adaptation for real-time personalization of an artificial pancreas," Expert Systems with Applications, vol. 42, Issue 4, Mar. 2015, pp. 2234-2255.
Yao et al., "Direct Policy Transfer via Hidden Parameter Markov Decision Processes," The 2nd Lifelong Learning: A Reinforcement Learning Approach (LLARLA) Workshop, Stockholm, Sweden, FAIM 2018, 7 pages.
Parbhoo et al., "Combining Kernel and Model Based Learning for HIV Therapy Selection," AMIA Joint Summits on Translational Science Proceedings, 2017, pp. 239-248.
Fox et al., "Reinforcement Learning for Blood Glucose Control: Challenges and Opportunities," Reinforcement Learning for Real Life (RL4RealLife) Workshop in the 36th International Conference on Machine Learning, Long Beach, California, 2019.
Luckett et al., "Estimating Dynamic Treatment Regimes in Mobile Health Using V-learning," 2017, 26 pages [retrieved from http://arxiv.org/abs/1611.03531v2].
Killian et al., "Robust and Efficient Transfer Learning with Hidden Parameter Markov Decision Processes," 31st Conference on Neural Information Processing Systems (NIPS 2017), Long Beach, CA, 12 pages.
Tordesillas et al., "Personalized Cancer Chemotherapy Schedule: a numerical comparison of performance and robustness in model-based and model-free scheduling methodologies," 2019, 8 pages, [retrieved from https://arxiv.org/ pdf/1904.01200.pdf].
Ahn et al., "Drug scheduling of cancer chemotherapy based on natural actor-critic approach," Biosystems, vol. 106, Issues 2-3, 2011, pp. 121-129.
Daskalaki et al., "Personalized tuning of a reinforcement learning control algorithm for glucose regulation," 2013 35th Annual International Conference of the IEEE Engineering in Medicine and Biology Society (EMBC), 2013, pp. 3487-3490.
Jalalimanesh et al., "Simulation-based optimization of radiotherapy: Agent-based modeling and reinforcement learning," Mathematics and Computers in Simulation, vol. 133, Mar. 2017, pp. 235-248.
Ngo et. al., "Reinforcement-learning optimal control for type-1 diabetes," 2018 IEEE EMBS International Conference on Biomedical & Health Informatics (BHI), 2018.
Padmanabhan et al., "Reinforcement learning-based control of drug dosing for cancer chemotherapy treatment," Math Biosciences, vol. 293, Nov. 2017, pp. 11-20.
Hassani et al., "Reinforcement Learning Based Control of Tumor Growth with Chemotherapy," 2010 International Coriference on System Science and Engineering, Aug. 2010, pp. 185-189.
Liu et al., "Deep Reinforcement Learning for Dynamic Treatment Regimes on Medical Registry Data," Healthc Inform., Aug. 2017, pp. 380-385.
Cruz-Lopez, "Deep Reinforcement Learning based Insulin Controller for Effective Type-1 Diabetic Care," MConf2019, New York City, [retrieved from https://mlconf.com/sessions/deep-reinforcement-learning-based-insulin-controller-for-effective-type-1-diabetic-care/].
"What is Continuous Glucose Monitoring (CGM)?" DEXCOPM Continuous Glucose Monitoring, 2021, 11 pages [retrieved from https://www.dexcom.com/continuous-glucose-monitoring on May 14, 2021].
Anonymous: "AI and Personalised Medicine Artificial Intelligence Technology, Media & Telecommunications United Kingdom International Law Finn CMS", Oct. 2, 2019 (Oct. 2, 2019), pp. 1-4, XP055805961, Retrieved from the Internet: URL:https ://cms.law/en/cze/publication/ai-and-personalisedmedicine.
Byrne S., et al., "Using Neural Nets for Decision Support in Prescription and Outcome Prediction in Anticoagulation Drug Therapy", Proceeding of Fifth International Workshop on Intelligent Data Analysis in Medicine and Pharmacology, Jan. 2020 pp. 7, XP055805964.
Extended European Search Report for Application No. EP20383037. 7, mailed on Jun. 1, 2021, 10 pages.

* cited by examiner

UTILIZING NEURAL NETWORK MODELS FOR RECOMMENDING AND ADAPTING TREATMENTS FOR USERS

CROSS-REFERENCE TO RELATED APPLICATION

This application claims priority to European Patent Application No. 20383037.7 entitled "UTILIZING NEURAL NETWORK MODELS FOR RECOMMENDING AND ADAPTING TREATMENTS FOR USERS," filed on Nov. 30, 2020. The entire content of which is expressly incorporated herein by reference.

BACKGROUND

Determining a treatment, for a user, is a difficult task that requires informed decisions of clinicians. Such a task may vary based on theoretical training of clinicians and may, therefore, be inconsistent and unreliable. Additionally, such a task may yield uncertain or unmeasured results.

SUMMARY

In some implementations, a method may include receiving user data identifying vitals of users when receiving treatments and dosages of the treatments, and processing the user data, with a divergence model, to determine divergence data identifying divergences between the users. The method may include processing the divergence data, with a clustering model, to group the users into clusters of users, and training a first neural network model, with the user data, to identify treatments for the clusters of users and to generate a trained first neural network model. The method may include training a second neural network model, with the user data, to determine outcomes for the treatments and to generate a trained second neural network model, and generating a treatment model based on the trained first neural network model and the trained second neural network model. The method may include training the treatment model with additional user data to generate a trained treatment model, and processing new user data identifying a new user, with the trained treatment model, to determine a recommended treatment for the new user. The method may include performing one or more actions based on the recommended treatment for the new user.

In some implementations, a device includes one or more memories and one or more processors to receive user data identifying vitals of users when receiving treatments and dosages of the treatments, wherein the user data includes one of historical user data identifying historical vitals of the users when receiving the treatments and historical dosages of the treatments, or simulated user data identifying simulated vitals of the users when receiving the treatments and simulated dosages of the treatments. The one or more processors may process the user data, with a divergence model, to determine divergence data identifying divergences between the users, and may process the divergence data, with a clustering model, to group the users into clusters of users. The one or more processors may train a first neural network model, with the user data, to identify treatments for the clusters of users and to generate a trained first neural network model, and may train a second neural network model, with the user data, to determine outcomes for the treatments and to generate a trained second neural network model. The one or more processors may generate a treatment model based on the trained first neural network model and the trained second neural network model, and may train the treatment model with additional user data to generate a trained treatment model. The one or more processors may process new user data identifying a new user, with the trained treatment model, to determine a recommended treatment for the new user, and may perform one or more actions based on the recommended treatment for the new user.

In some implementations, a non-transitory computer-readable medium may store a set of instructions that includes one or more instructions that, when executed by one or more processors of a device, cause the device to receive user data identifying vitals of users when receiving treatments and dosages of the treatments, and process the user data, with a divergence model, to determine divergence data identifying divergences between the users. The one or more instructions may cause the device to process the divergence data, with a clustering model, to group the users into clusters of users, and train a first neural network model, with the user data, to identify treatments for the clusters of users and to generate a trained first neural network model. The one or more instructions may cause the device to train a second neural network model, with the user data, to determine outcomes for the treatments and to generate a trained second neural network model, and generate a treatment model based on the trained first neural network model and the trained second neural network model. The one or more instructions may cause the device to train the treatment model with additional user data to generate a trained treatment model, and process new user data identifying a new user, with the divergence model, to determine new divergence data identifying a divergence of the new user. The one or more instructions may cause the device to process the new divergence data, with the clustering model, to assign the new user to one of the clusters of users, and process the new user data, with the trained treatment model, to determine a recommended treatment for the new user based on the one of the clusters of users assigned to the new user. The one or more instructions may cause the device to perform one or more actions based on the recommended treatment for the new user.

DETAILED DESCRIPTION

Figure 1A:
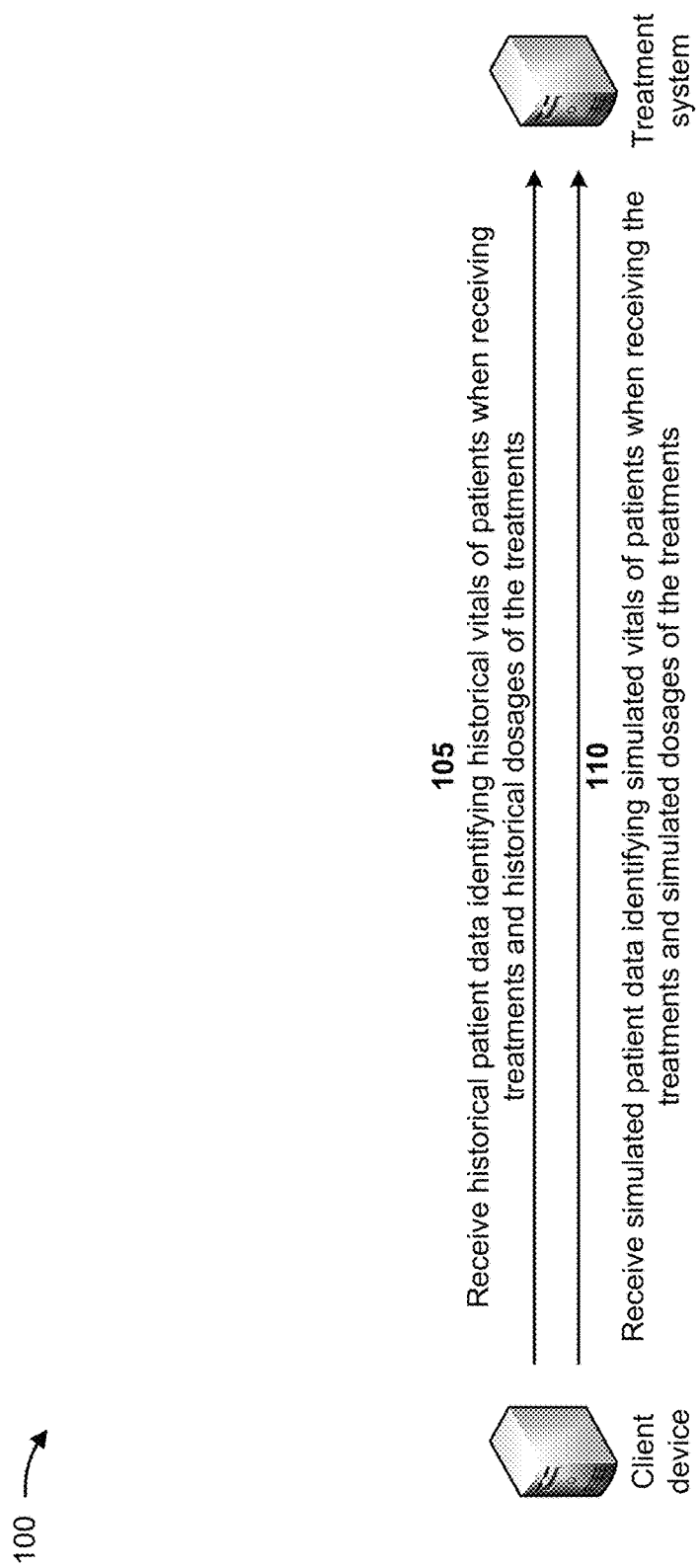
FIGS. 1A-1F are diagrams of an example implementation described herein.

The following detailed description of example implementations refers to the accompanying drawings. The same reference numbers in different drawings may identify the same or similar elements.

There are different ways to identify and select treatments for users. One approach is largely based on theoretical posture and personal experience of a clinician. Another approach relies on treatments supported by empirical data and simulated data. However, this approach ignores variations from one user to another user. Some approaches provide a distinction between a standard protocol or a (subjective) expert decision that typically determines a treatment and a potential adaptation to a particular user with data and objective methods. Current approaches may use multiple devices to identify and select the treatments for the users and sometimes the selected treatments are inappropriate for some users. Thus, current approaches for selecting treatments for users wastes computing resources (e.g., processing resources, memory resources, communication resources, and/or the like), networking resources, and/or other resources associated with selecting inappropriate treatments for users, implementing the inappropriate treatments, identifying that the treatments are inappropriate, and/or performing another action to address the inappropriate treatments.

Some implementations described herein relate to a treatment system that utilizes neural network models for recommending and adapting treatments for users. For example, the treatment system may receive user data identifying vitals of users when receiving treatments and dosages of the treatments, and may process the user data, with a divergence model, to determine divergence data identifying divergences between the users. The treatment system may process the divergence data, with a clustering model, to group the users into clusters of users, and may train a first neural network model, with the user data, to identify treatments for the clusters of users and to generate a trained first neural network model. The treatment system may train a second neural network model, with the user data, to determine outcomes for the treatments and to generate a trained second neural network model, and may generate a treatment model based on the trained first neural network model and the trained second neural network model. The treatment system may train the treatment model with additional user data to generate a trained treatment model, and may process new user data identifying a new user, with the trained treatment model, to determine a recommended treatment for the new user. The treatment system may perform one or more actions based on the recommended treatment for the new user. In some implementations, the treatment model may be implemented using a reinforcement learning model in which the first neural network model and the second neural network model are trained at the same time.

By using the trained treatment model, the treatment system conserves computing resources, networking resources, and/or other resources that would have otherwise been wasted in selecting inappropriate treatments for users, implementing the inappropriate treatments, identifying that the treatments are inappropriate, and/or performing another action to address the inappropriate treatments.

FIGS. 1A-1F are diagrams of an example implementation 100 described herein. Example implementation 100 may be associated with utilizing neural network models for recommending and adapting treatments for users. As shown in FIGS. 1A-1F, example implementation 100 includes a client device associated with a treatment system. The client device may include a laptop computer, a mobile telephone, a desktop computer, and/or similar device utilized by a user. The treatment system may include a server device or a collection of server devices (e.g., associated with a cloud computing environment or a data center) that utilizes neural network models for recommending and adapting treatments for users. The user device and the treatment system are described in more detail below in connection with FIG. 3 and FIG. 4.

In the description to follow and simply as an example, assume the treatment system has received (e.g., from the client device and/or from another device) a treatment request to recommend and/or adapt a treatment for a new user. While some instances of the example may refer to treatment of a particular medical condition (e.g., diabetes), the description herein is applicable to the treatment of other medical conditions.

As described in more detail below, the treatment system may recommend and/or adapt the treatment for a new user based on user data of one or more users (e.g., historical user data and/or simulated user data) and based on new user data of the new user. Any collection, storage, and use of user data is subject to consent of a respective user to such activity and may be in accordance with all applicable laws concerning protection of personal information. Storage and use of such user data are done in an appropriately secure manner reflective of the type of such user data.

As shown in FIG. 1A, and by reference number 105, the treatment system may receive historical user data identifying historical vitals of users when receiving treatments and historical dosages of the treatments. For example, the treatment system may receive the historical user data from the client device. In some implementations, the treatment system may receive the historical user data based on receiving the treatment request. For example, the treatment system may receive the historical user data from the client device as part of receiving the treatment request from the client. In some implementations, the treatment system may receive the treatment request from another device (e.g., a device of a user associated with the treatment system) and may transmit a user data request to the client device based on receiving the treatment request. The treatment system may receive the historical user data, from the client device, based on transmitting the user data request.

In some implementations, the vitals may include variables such as blood pressures, heart rates, blood oxygen levels, blood glucose levels, blood cholesterol levels, and/or other vitals for users. In some examples, the vitals may include continuous variables (e.g., a vector of continuous variables such as blood pressure over a period of time) and/or discrete variables (e.g., a vector of discrete variables such as postprandial vitals). In some implementations, the historical vitals of users may include vitals (of users), measured by one or more devices, after and/or prior to the users receiving the treatments and the historical dosages of the treatments.

In some implementations, the historical user data may further include user information identifying the users, include treatment information identifying the treatments and/or the historical dosages of the treatments, and/or include outcome information identifying outcomes of the treatments being administered to the users (e.g., administered in accordance with the historical dosages of the treatments). In some implementations, the user information may include information identifying an age, a weight, a height, dietary/nutritional information (e.g., information identifying meals), workout/exercise information (e.g., information identifying an amount of exercise per time period), and/or medical conditions (e.g., diabetes) of a user.

In some implementations, a treatment may include one or more actions taken (e.g., by medical personnel such as a clinician) to maintain and/or improve the health of users (e.g., maintain and/or improve the vitals of the users) and/or may include a frequency at which the one or more actions are taken. An example of a treatment may include administering medication (e.g., insulin) on a daily basis. In some instances, the one or more actions may include administering the medication (e.g., the insulin) to a user. The one or more actions may be continuous actions and/or discrete actions. The continuous actions may include actions occurring over an extended period of time (e.g., administering a treatment every period of time (e.g., every three minutes)). Discrete actions may include actions occurring at discrete times (e.g., administering a treatment (e.g., insulin) after certain meals). In some implementations, a dosage of a treatment may include a dosage of medication administered to a user. In some implementations, the dosage of the treatment may be a continuous value (e.g., a range of value such as 0 to 5 mg/l). Additionally, or alternatively, the dosage of the treatment may be discrete (e.g., a choice between a dosage of 1 mg/l, 2 mg/l, 3 mg/l or 4 mg/l).

In some implementations, the outcome information may include information indicating whether administering a treatment (e.g., in accordance with a dosage of the treatment) is successful and/or includes information identifying a measure of success associated with administering the treatment. In some examples, the measure of success may be based on a measure of improvement of the vitals (described above) after the treatment is administered and/or a reduction of exposure to a risk associated with the medical condition.

By way of example of the different types of information described above, the historical user data may include first user information of a first user, first treatment information for the first user, and first outcome information associated with the first treatment information for the first user. The historical user data may further include second user information of a second user, second treatment information for the second user, and second outcome information relating to the second treatment information for the second user. The historical user data may include similar information for one or more other users (e.g., hundreds, thousands, millions, or more additional users).

As shown in FIG. 1A, and by reference number 110, the treatment system may receive simulated user data identifying simulated vitals of users when receiving the treatments and simulated dosages of the treatments. For example, the treatment system may receive the simulated user data from the client device in a manner similar to the manner described above in connection with receiving the historical user data.

In some implementations, the simulated vitals (of users (e.g., synthetic users)) may include vitals (of users), simulated using one or more simulation models, after and/or prior to the users receiving the treatments and the historical dosages of the treatments. The one or more simulation models may include one or more models that simulate vitals of users after and/or prior to the users receiving the treatments and the historical dosages of the treatments. In some instances, the one or more simulation models may receive, as input, user information of such users. The one or more simulation models may provide, as output, the simulated vitals of the users. For example, the one or more simulation models may receive, as input, user information of a user and may provide, as output, the simulated vitals of the user.

In some implementations, the simulated user data may further include the user information of the users (as described above in connection with reference number 105), include treatment information of the treatments and/or the dosages of the treatments (as described above in connection with reference number 105), and/or include outcome information identifying outcomes of the treatments administered to the users (as described above in connection with reference number 105). In some instances, the one or more simulation models may receive, as input, user information of a user and/or treatment information of a user and may provide, as output, outcome information of the user. As an example, the treatment information of the user may include administering a medication (e.g., insulin) after every meal and the outcome information of the user may indicate a reduction of a blood glucose level and/or indicate a reduction of risk (associated with a medical condition (e.g., diabetes) of the user) after receiving the treatment.

In some implementations, the simulated user data may include information identifying one or more benchmark policies relating to a correlation between one or more of the treatments (administered in accordance with the dosages of the one or more of the treatments) and corresponding one or more of the outcomes. For example, the benchmark policy (associated with a treatment) may indicate a manner in which the treatment affects the health of the users (e.g., affects the simulated vitals of the synthetic users).

In some implementations, the treatment system may receive the simulated user data without receiving the historical user data. In some implementations, the treatment system may receive the historical user data without receiving the simulated user data. In some implementations, the treatment system may receive the simulated user data in conjunction with receiving the historical user data.

Figure 1B:
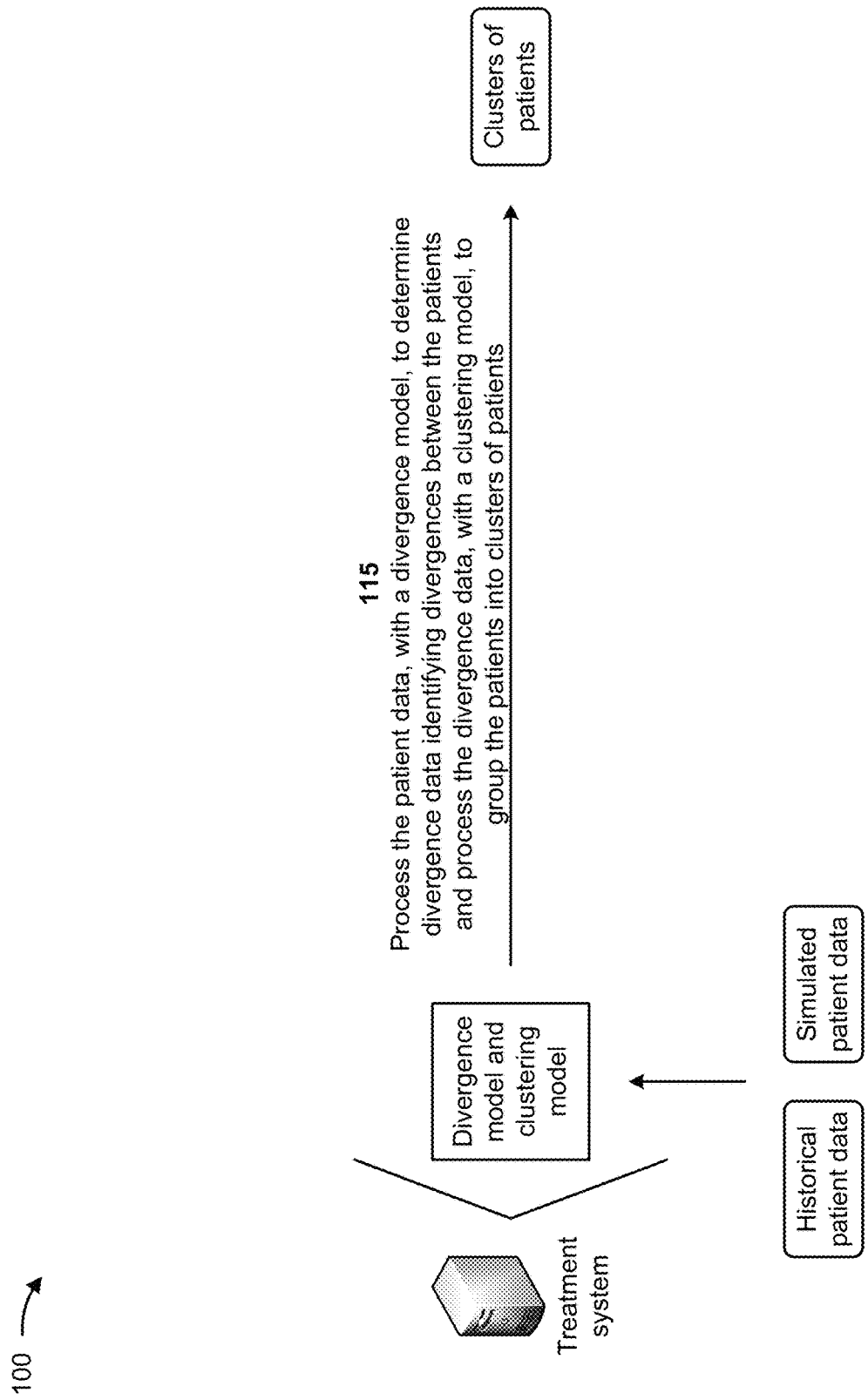

As shown in FIG. 1B, and by reference number 115, the treatment system may process the user data, with a divergence model, to determine divergence data identifying divergences between the users and process the divergence data, with a clustering model, to group the users into clusters of users. For example, after receiving the historical user data and/or the simulated user data from the client device, the treatment system may process the user data (e.g., the historical user data and/or the simulated user data) with the divergence model to determine the divergence data identifying the divergences between the users.

In some implementations, the divergence model may include a model that uses a kernel density estimation (KDE) and a Jensen-Shannon method to determine divergences between the users. In some examples, the treatment system may use KDE to generate multinomial distributions of data (e.g., historical user data) that define the users. As an example, a user may be defined based on information identifying vitals of the user and treatment information of the user.

The treatment system may determine (e.g., calculate or compute) a pairwise Jensen-Shannon (JS) divergences between the users (e.g., defined using the KDE). As an example, the JS divergence between a pair of users (e.g., a first user and a second user) may indicate a distance between historical user data of the first user and historical user data of the second user. A measure of divergence between the pair of users may increase as a magnitude of the JS divergence between the pair of users increases. Conversely, a measure of similarity between the pair of users may increase as a magnitude of the JS divergence between the pair of users decreases. The treatment system may generate a distance matrix based on the pairwise Jensen-Shannon divergences between the users. In some examples, the distance matrix may correspond to the divergence data.

The treatment system may process the divergence data (described above), with the clustering model, to group the users into the clusters of users. In some implementations, the clustering model may include a hierarchical clustering model. When processing the divergence data with the clustering model, the treatment system may apply the hierarchical clustering model to the divergence data to group the users into the clusters of users. For example, the treatment system may provide the divergence data as input to the hierarchical clustering model and the hierarchical clustering model may generate, as an output, the clusters of users. The hierarchical clustering model is merely provided as an example, and other types of clustering models may be used.

In some examples, a first pair of users may be included in a same cluster when the measure of similarity between the first pair of users satisfies a similarity threshold (or fails to satisfy a divergence threshold described below). The similarity threshold may correspond to a value (e.g., a value of a JS divergence) that indicates that users are similar (and, accordingly, are to be included in a same cluster). In some implementations, information identifying the similarity threshold may be included in the treatment request and the treatment system may determine the similarity threshold based on the information identifying the similarity threshold. Additionally, or alternatively, the treatment system may determine the similarity threshold based on historical data (e.g., historical divergence data).

A second pair of users may be included in different clusters when the measure of divergence between the second pair of users satisfies a divergence threshold (or fails to satisfy the similarity threshold). The divergence threshold may correspond to a value (e.g., a value of a JS divergence) that indicates that users are dissimilar (and, accordingly, are to be included in different clusters). In some implementations, information identifying the divergence threshold may be included in the treatment request and the treatment system may determine the divergence threshold based on the information identifying the divergence threshold. Additionally, or alternatively, the treatment system may determine the divergence threshold based on historical data (e.g., historical divergence data).

In some implementations, a cluster of users may be specific with respect to (or may be associated with) a condition. Additionally, or alternatively, a cluster of users may be specific with respect to (or may be associated with) a symptom of one or more conditions. In some implementations, the divergence model and/or the clustering model may be trained and/or implemented on the treatment system. In some implementations, the divergence model and/or the clustering model may be trained and/or implemented on another system or device.

Figure 1C:
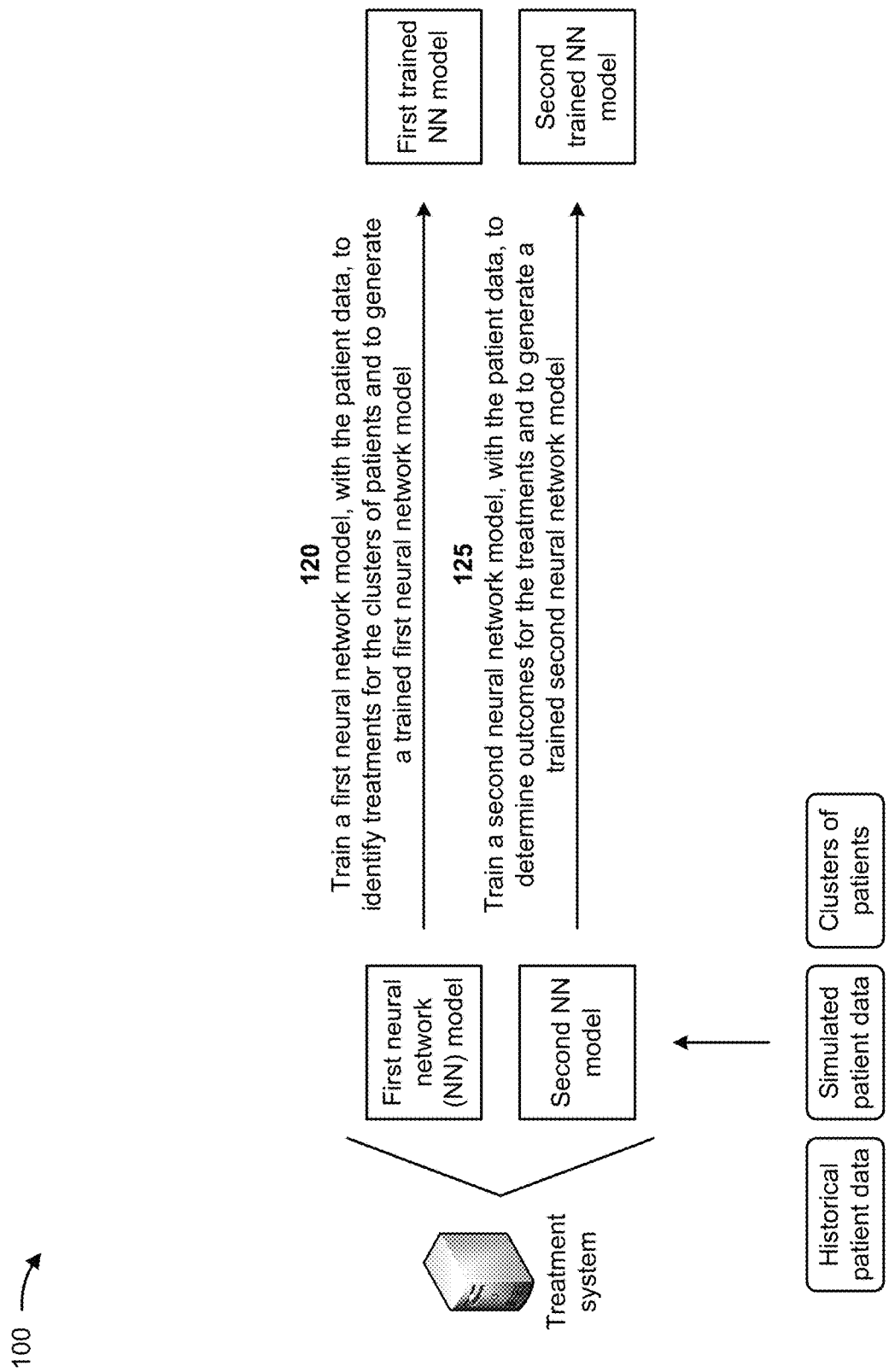

As shown in FIG. 1C, and by reference number 120, the treatment system may train a first neural network model, with the user data, to identify treatments for the clusters of users and to generate a trained first neural network model. In some implementations, the treatment system may select the historical user data and/or the simulated user data as the user data based on a preference relating a type of user data (historical user data and/or simulated user data) to be used for training the first neural network model. In some examples, information regarding the preference may be included in the treatment request and the treatment system may determine the preference based on the treatment request. Additionally, or alternatively, the treatment system may determine the preference based on historical data (e.g., historical preferences and/or historical treatment requests).

In some implementations, the treatment system may train the first neural network model, with the user data, to identify treatments (and/or dosage of the treatments) for the clusters of users based on analyzing the user data. For example, the treatment system may train the first neural network to identify or predict a first treatment (and/or a first dosage for the first treatment) for a first cluster of users based on analyzing a first portion of the user data associated with the first cluster of users, identify or predict a second treatment (and/or second dosage for the second treatment) for a second cluster of users based on analyzing a second portion of the user data associated with the second cluster of users, and so on. In some implementations, the first treatment (and/or the first dosage for the first treatment) may correspond to a first treatment policy (or a first baseline treatment policy) for the first cluster of users, the second treatment (and/or the second dosage for the second treatment) may correspond to a second treatment policy (or a second baseline treatment policy) for the second cluster of users, and so on.

The first portion of the user data may include user information of users of the first cluster of users, information identifying vitals of the users of the first cluster of users, and/or treatment information for the users of the first cluster of users. The second portion of the user data may include user information of users of the second cluster of users, information identifying vitals of the users of the second cluster of users, and/or treatment information for the users of the second cluster of users.

In some implementations, when training the first neural network model, the treatment system may calculate variances associated with the treatments for the clusters of users and may generate the trained first neural network model when the variances satisfy a threshold variance and when an explanation exists for the variances (e.g., when the variances can be explained by the first neural network model). For example, the treatment system may calculate a variance associated with the first treatment for the first cluster of users (e.g., a variance associated with treatments identified in the first portion of the user data and/or a variance associated with the dosages of the treatments), a variance associated with the second treatment for the second cluster of users, and so on. The treatment system may determine whether the variances satisfy the threshold variance. The threshold variance may be determined in manner similar to the manner in which the similarity threshold and the divergence threshold are determined (e.g., based on the treatment request and/or based on the historical data). As an example, the threshold variance may be more than fifty percent.

In some examples, when the variances (associated with the first treatment) satisfy the threshold variance, the treatment system may determine whether an explanation exists for the variances (e.g., determine whether the variances can be addressed by the first neural network model). In some instances, when determining whether the variances can be addressed by the first neural network, the treatment system may determine whether the first treatment addresses the variance associated with the first treatment, whether the second treatment addresses the variance associated with the second treatment, and so on.

If the treatment system determines that an explanation exists for the variances (e.g., for the variance associated with the first treatment, the variance associated with the second treatment, and so on), the treatment system may determine that the first neural network has been trained. If the treatment system determines that an explanation does not exist for the variances, the treatment system may adjust the first treatment, adjust the second treatment, and so on until the treatment system determines that an explanation exists for the variances associated with adjusted treatments (e.g., the variance associated with an adjusted first treatment, the variance associated with an adjusted second treatment, and so on).

In some implementations, the first neural network model may be trained as described below in connection with FIG. 2. The first neural network model may be trained to determine the treatments (and/or dosage of the treatments), identified in the user data, for users that are included in the cluster of users. As explained above, the treatment system may train the first neural network model.

In some implementations, rather than training the first neural network model, the treatment system may obtain the trained first neural network model from another system or device that trained the first neural network model to generate the trained first neural network model. In this case, the treatment system may provide the other system or device with the user data for use in training the first neural network model, and/or may provide the other system or device with user data to retrain the first neural network model in order to update the trained first neural network model. In some implementations, the first neural network model may include a long short-term memory model, a time-series model, a neural network with logistic regression model, and/or another similar type of model.

In some examples, the trained first neural network model may receive, as input, particular user data of a particular user and/or information identifying a particular cluster of users (to which the particular user is assigned) and may generate, as an output, a predicted treatment (and/or dosage of the predicted treatment) for the particular user (e.g., based on the particular user being assigned to the particular cluster of users).

As shown in FIG. 1C, and by reference number 125, the treatment system may train a second neural network model, with the user data, to determine outcomes for the treatments and to generate a trained second neural network model. For example, the treatment system may train the second neural network model, with the user data, to determine or identify the outcomes associated with administering the treatments (e.g., in accordance with the dosages of the treatments) to users of the clusters of users based on the second neural network model analyzing the user data.

As explained above, the outcomes may indicate whether administering the treatments (e.g., in accordance with the dosages of treatments) is successful and indicate a measure of success relating to administering the treatments. The trained second neural network may receive, as input, particular user data of a particular user (e.g., treatment information of the particular user) and may provide, as an output, a predicted outcome associated with administering a treatment (identified by the treatment information) to the particular user.

In some implementations, the treatment system may train the second neural network to identify or predict a first outcome (e.g., associated with administering treatments) for a first cluster of users based on analyzing a third portion of the user data associated with the first cluster of users, identify or predict a second outcome (e.g., associated with administering treatments) for a second cluster of users based on analyzing a fourth portion of the user data associated with the second cluster of users, and so on.

The third portion of the user data may include outcome information for the users of the first cluster of users, treatment information for the users of the first cluster of users, the information identifying vitals of the users of the first cluster of users, and/or the user information of users of the first cluster of users. The fourth portion of the user data may include outcome information for the users of the second cluster of users, treatment information for the users of the second cluster of users, the information identifying vitals of the users of the second cluster of users, and/or the user information of users of the second cluster of users. The first portion of the user data may be a subset of the third portion of the user data and the second portion of the user data may be a subset of the fourth portion of the user data.

In some implementations, when training the second neural network model, the treatment system may calculate variances associated with the outcomes for the treatments and may generate the trained second neural network model when the variances satisfy the threshold variance and when an explanation exists for the variances (e.g., when the variances can be addressed by the second neural network model), in a manner similar to the manner described above in connection with the variances of the treatments.

In some implementations, the second neural network model may be trained as described below in connection with FIG. 2. As explained above, the treatment system may train the second neural network. In some implementations, rather than training the first neural network model, the treatment system may obtain the trained second neural network model from another system or device that trained the second neural network model to generate the trained second neural network model, in a manner similar to the manner described above in connection with the trained first neural network. In some implementations, the second neural network model may include a long short-term memory model, a time-series model, a neural network with logistic regression model, and/or another similar type of model. In some implementations, the treatment system may train the first neural network and/or the second neural network, as described herein, for treatments associated with discrete actions. For example, the treatment system may determine a baseline treatment policy for treatments associated with discrete actions.

Figure 1D:
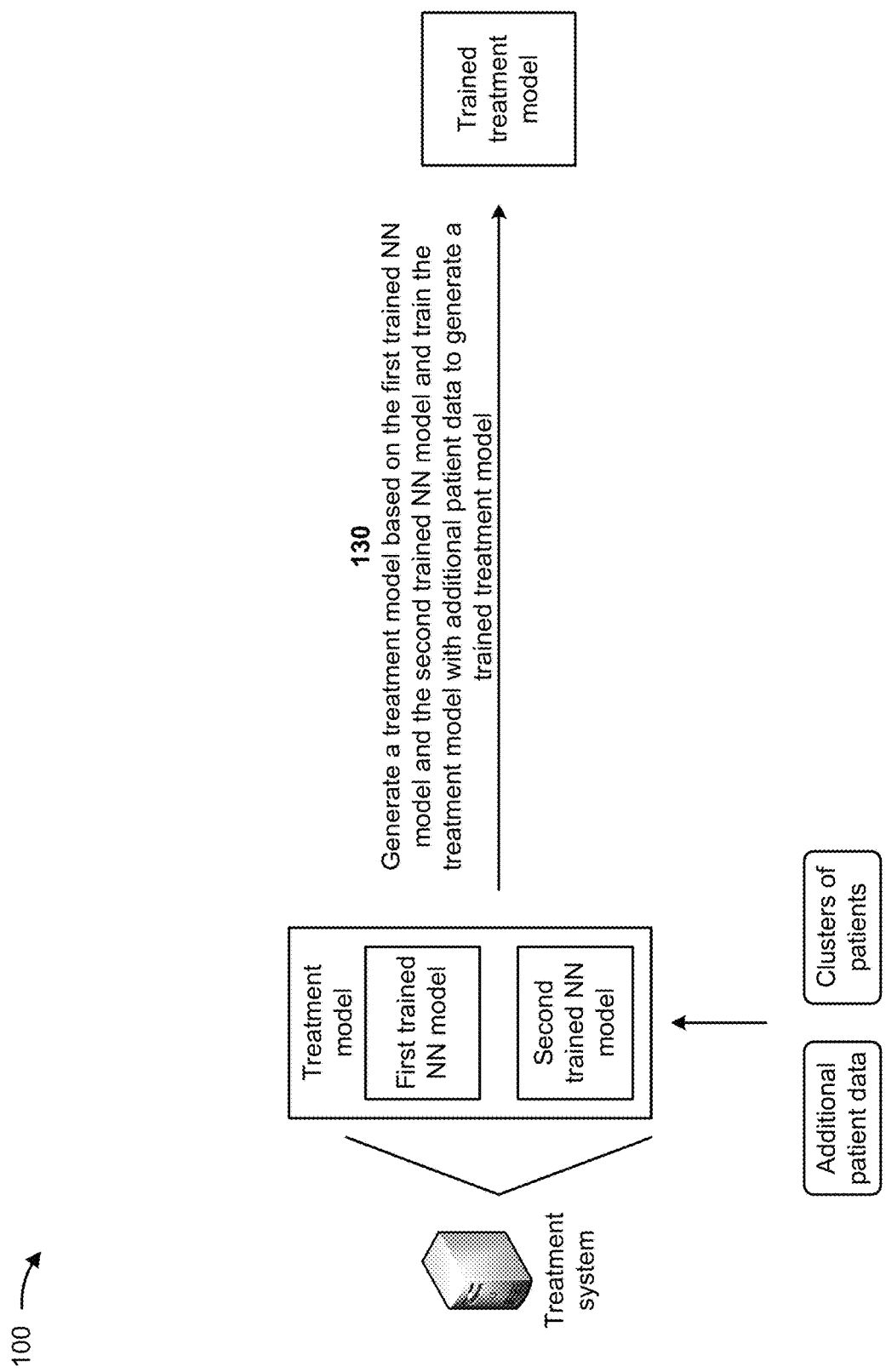

As shown in FIG. 1D, and by reference number 130, the treatment system may generate a treatment model based on the trained first neural network model and the trained second neural network model and train the treatment model with additional user data to generate a trained treatment model. For example, the treatment system may generate the treatment model as a model that includes the trained first neural network model and the trained second neural network model. For instance, the treatment model may receive, as an input, particular user data (of a particular user) and/or information identifying a particular cluster of users to which the particular user is to be assigned and may generate or predict, as an output, information identifying a particular treatment for the particular user (e.g., the particular treatment associated with the particular cluster) and/or information identifying a predicted outcome of administering the particular treatment to the particular user.

In some implementations, the treatment system may obtain additional user data. The treatment system may obtain the additional user data to further train (or retrain) the trained first neural network model and the trained second neural network model and, thereby, to optimize the trained first neural network model and the trained second neural network model.

In some implementations, the treatment system may obtain the additional user data by altering information included in the user data (discussed above) and causing (e.g., using the one or more simulation models discussed above) a simulation of outcomes based on the altered information. In some examples, the treatment system may transmit (e.g., to the client device) a simulation request (e.g., including the user data with the altered information) to cause the simulation to be performed and may receive (e.g., from the client device) an output of the simulation. The additional user data may include the altered information and/or an output of the simulation of the outcomes based on the altered information.

With respect to the first cluster of users, as an example, the treatment system may alter information regarding the first treatment (e.g., alter the first treatment and/or alter the dosage of the first treatment) and may cause a simulation of an outcome based on the altered information. The treatment system may determine whether the simulated outcome is an improvement of the first outcome for the first cluster of users. If the treatment system determines that the simulated outcome is an improvement, the treatment system may cause the treatment model to be trained (or retrained) using the altered information and/or an output of the simulation (e.g., information regarding the simulated outcome). In such instance, the altered information and/or the output of the simulation may be part of the additional data.

In some examples, the treatment system may cause the first neural network model to be retrained based on the altered information (e.g., to cause the first treatment to be updated based on the altered information). The treatment system may cause the second neural network model to be retrained based on the output of the simulation (e.g., to cause the first outcome to be updated based on the output of the simulation). Retraining the first neural network model and the second neural network model in this manner optimizes the first baseline treatment policy associated with the first cluster of users. If the treatment system determines that the simulated outcome is not an improvement, the treatment system may repeat the alteration and the simulation until the treatment system identifies a simulated outcome that is an improvement of the first outcome for the first cluster of users. The treatment system may perform similar actions for one or more other clusters of users to optimize the baseline treatment policies associated with the other cluster of users.

Figure 1E:
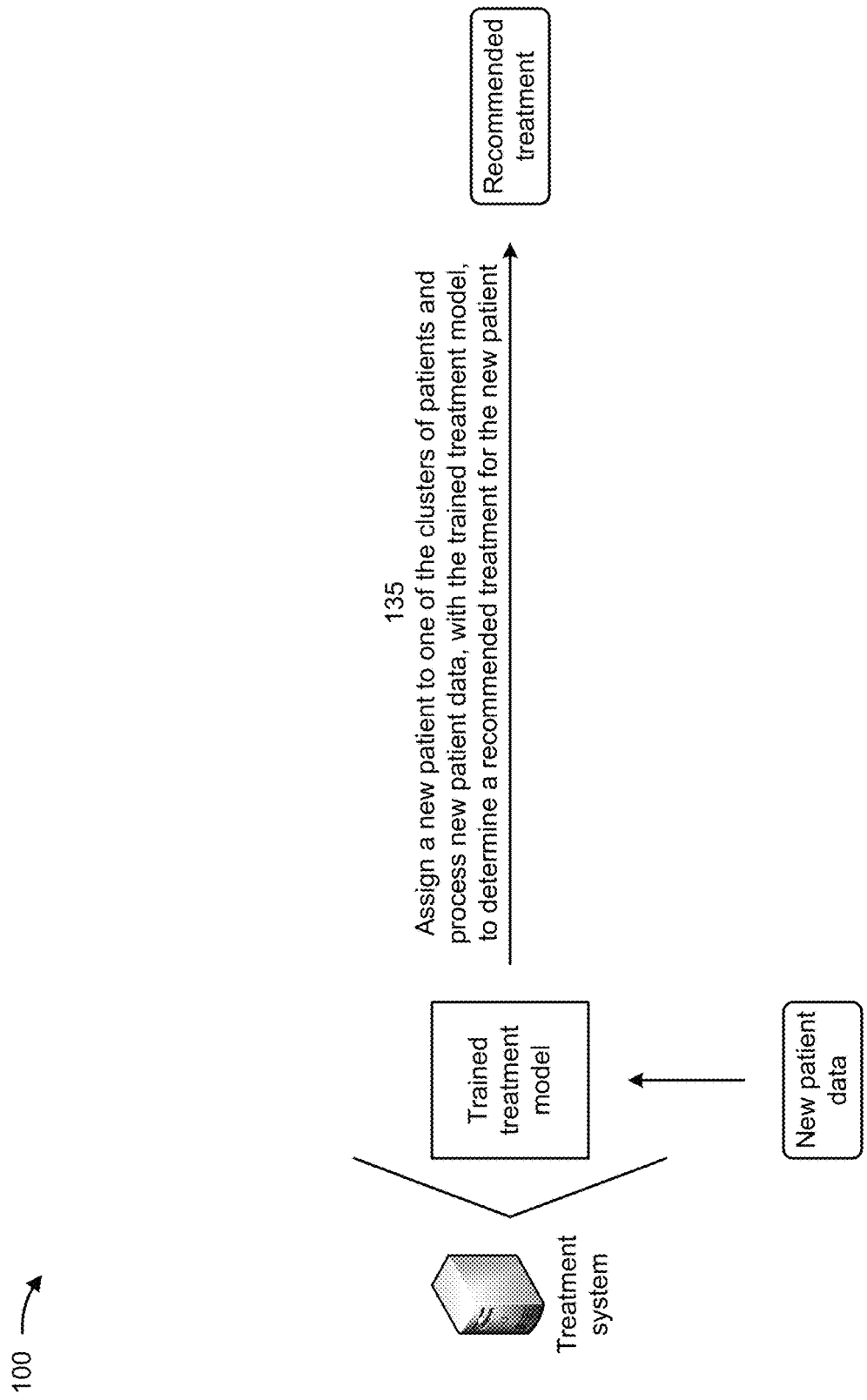

As shown in FIG. 1E, and by reference number 135, the treatment system may assign a new user to one of the clusters of users and process new user data, with the trained treatment model, to determine a recommended treatment for the new user. For example, prior to processing the new user data with the trained treatment model, the treatment system may process the new user data, with the divergence model, to determine new divergence data identifying a divergence of the new user (e.g., with respect to one or more users of the clusters of users), in a manner similar to the manner described above in connection with reference number 115. The new user data may include information similar to the user data described above (e.g., user information of the new user, information identifying vitals of the new user, historical treatment information of the new user, and/or historical outcome information of the new user).

Prior to processing the new user data with the trained treatment model, the treatment system may process the new divergence data, with the clustering model, to assign the new user to a cluster of users from the clusters of users, in a manner similar to the manner described above in connection with reference number 115. The treatment system (e.g., using the trained treatment model) may determine a recommended treatment for the new user. For example, the treatment system may provide, as input to the trained treatment model, information identifying the cluster of users (to which the new user is assigned). The trained treatment model may identify, based on the information identifying the cluster of users, a treatment for the cluster of users and may provide, as an output, the treatment for the cluster of users as the recommended treatment for the new user. In some implementations, the treatment model may be implemented using a reinforcement learning model in which the first neural network model and the second neural network model are trained at the same time. In some examples, based on reinforcement learning techniques of the reinforcement model, the recommended treatment for the new user will be identified and will be updated over a period of time (as explained below), based on the treatment model being retrained (or learning) based on an outcome of the recommended treatment being administered to the new user.

In some examples, the recommended treatment may include a continuous action, as described above. Alternatively, the recommended treatment may include a discrete action, as described above.

Figure 1F:
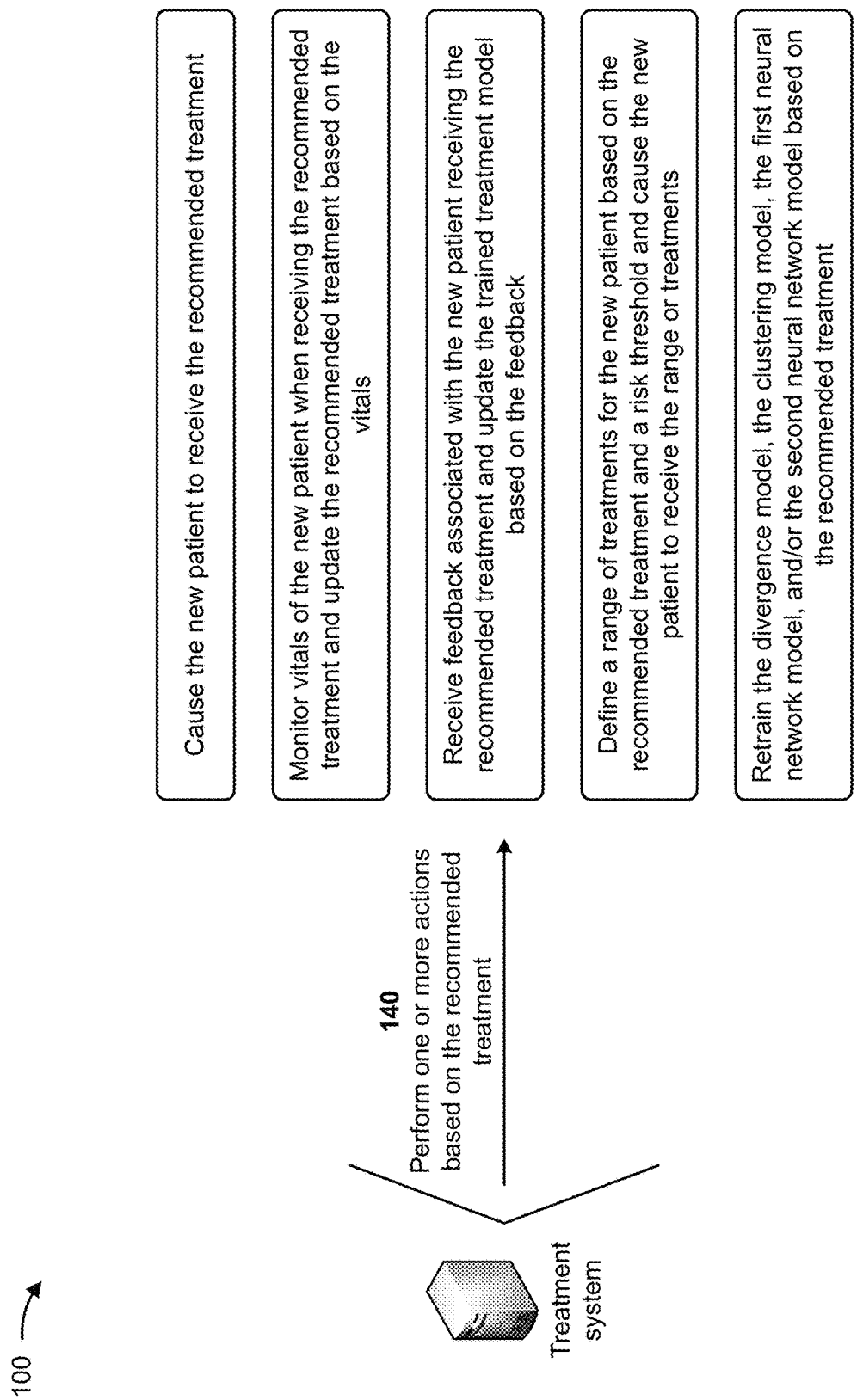

As shown in FIG. 1F, and by reference number 140, the treatment system may perform one or more actions based on the recommended treatment. In some implementations, the one or more actions may include the treatment system causing the new user to receive the recommended treatment. For example, the treatment system may cause the new user to receive the recommended treatment and cause the recommended treatment to be implemented for the new user. In some instances, the treatment system may transmit a notification to a device (e.g., an autonomous device) to cause the device to navigate to a location of the new user and deliver the recommended treatment (e.g., the medication) at the location of the new user. For example, the new user data may include information identifying the location of the new user. The notification may include user information of the new user, the information identifying the location of the new user, and treatment information associated with the recommended treatment. In some implementations, the notification may cause the device (or another device) to administer the recommended treatment to the new user.

In some implementations, the device may be a device of an individual (e.g., a medical support staff, a doctor of the new user, a delivery personnel, a relative of the new user, and/or a friend of the new user). In some instances, the new user data may include information identifying the device (e.g., a telephone number of the device and/or a network address of the device). The treatment system may transmit the notification to the device of the individual to cause the individual to deliver the recommended treatment to the location of the new user and/or cause the individual to administer the recommended treatment to the new user.

In some implementations, the one or more actions may include the treatment system monitoring vitals of the new user when receiving the recommended treatment and updating the recommended treatment based on the vitals. For example, the treatment system may receive information identifying the vitals from a device (e.g., the client device, a device of the new user, a device of a medical personnel associated with the new user, and/or a device of an individual associated with the new user) when the new user is receiving the recommended treatment and/or after the new user receives the recommended treatment. The treatment system may analyze the information identifying the vitals to determine any changes with respect to the vitals as and/or after the new user receives the recommended treatment. The treatment system may update the recommended treatment based on the changes to the vitals.

For example, the treatment system may cause a dosage of the recommended treatment to be increased and/or a frequency of administering the recommended treatment to be increased if the vitals are not improving and/or are worsening. Alternatively, the treatment system may cause the dosage of the recommended treatment to be decreased and/or a frequency of administering the recommended treatment to be decreased if the vitals are improving. In some implementations, the treatment system may cause the treatment model, the first neural network model, and/or the second neural network model to be retrained based on information identifying the updated recommended treatment.

Updating the recommended treatment based on the vitals may conserve computing resources, network resources, and/or other resources that would have otherwise been used to provide treatments because the updated recommend treatment may be more accurate by being updated based on the vitals.

In some implementations, the one or more actions may include the treatment system receiving feedback associated with the new user receiving the recommended treatment and updating the trained treatment model based on the feedback. For example, the treatment system may receive outcome information identifying outcomes associated with the new user receiving the recommended treatment (e.g., receiving the recommended treatment over a period of time). For instance, the treatment system may receive first outcome information after the new user receives the recommended treatment a first time, receive second outcome information after the new user receives the recommended treatment a second time, and so on. In some examples, the treatment system may receive the outcome information (e.g., the first outcome information, the second information, and so on) from the device (e.g., the client device, the device of the new user, the device of a medical personnel associated with the new user, and/or the device of an individual associated with the new user).

The treatment system may analyze the outcome information (e.g., after the recommended treatment has been administered a threshold number of times) to determine any changes with respect to the vitals of the new user. The treatment system may determine changes to the recommended treatment based on the changes with respect to the vitals of the new users. For example, the treatment system may cause a dosage of the recommended treatment to be increased and/or a frequency of administering the recommended treatment to be increased if the vitals are not improving and/or are worsening. Alternatively, the treatment system may cause the dosage of the recommended treatment to be decreased and/or a frequency of administering the recommended treatment to be decreased if the vitals are improving.

The treatment system may adapt the trained treatment model for the new user based on the outcome information and determine an updated recommended treatment for the new user based on adapting the trained treatment model for the new user. For example, the treatment system may train (or retrain) the trained treatment model, in a manner similar to the manner described herein, based on information regarding the changes to the recommended treatment and/or based on the outcome information. In some implementations, the treatment system may cause the trained treatment model to be trained to identify or determine the updated recommended treatment for the new user based on the changes to the recommended treatment. In some instances, the update recommended treatment may be a replacement for or an alternative to the recommended treatment for the cluster of users to which the new user is assigned.

The treatment system may cause the updated recommended treatment to be implemented for the new user. For example, the treatment system may cause the updated recommended treatment to be administered to the new user, in a manner similar to the manner explained above. The treatment system may monitor vitals of the new user when receiving the updated recommended treatment and further update the updated recommended treatment based on monitoring the vitals, in a manner similar to the manner explained above.

Updating the trained treatment model based on the feedback may conserve computing resources, network resources, and/or other resources that would have otherwise been used to provide future recommended treatments as the future recommend treatments may be more accurate because of the feedback.

In some implementations, the one or more actions may include the treatment system defining a range of treatments for the new user based on the recommended treatment and a risk threshold and causing the new user to receive the range of treatments. For example, the treatment system may use the recommended treatment as a baseline treatment and determine a standard of deviation with respect to the recommended treatment. In some instances, the treatment system may determine a difference between the recommended treatment and historical treatment data of the new user (e.g., the treatment information included in the new user data and/or information regarding the updated recommended treatment discussed above).

The treatment system may determine the standard of deviation based on the difference and may determine the range of treatments based on the standard of deviation with respect to the recommended treatment. For example, the range of treatments may include a range of dosage and/or a range of time periods for administering a treatment. By determining the standard of deviation based on the difference, the treatment system may ensure that the range of treatments do not satisfy the risk threshold. The risk threshold may be associated with a treatment that may cause unintended consequences to the new user. The risk threshold may be determined in a manner similar to the manner described herein with respect to other thresholds. The treatment system may cause the new user to receive the range of treatments, in a manner similar to the manner described above.

In some implementations, the one or more actions may include the treatment system retraining the divergence model, the clustering model, the first neural network model, and/or the second neural network model based on the recommended treatment. Additionally, or alternatively, the models may be retrained based on any updates to the recommended treatment and/or based on outcome information associated the recommended treatments and/or associated with any updates to the recommended treatments. By retraining the divergence model, the clustering model, the first neural network model, and/or the second neural network model, the treatment system may improve the accuracy of the models in determining a cluster of users for a user, in recommending a treatment for a user, and/or predicting an outcome associated with administering a treatment to a user. Improving the accuracy of the models may improve speed and efficiency of the models, and thereby conserve computing resources, networking resources, and/or similar resources that would have otherwise been used by slower and less efficient models.

The treatment system utilizes neural network models for recommending and adapting treatments for users so that treatment policies for individual users are improved. The treatment system recommends treatment dosages for a new user and learns from specific outcomes for the new user so that the treatment for the new user may be optimized and adapted over time for the new user. By optimizing and adapting the treatment for the new user, the treatment system conserves computing resources, networking resources, and/or other resources that otherwise would have been used by inferior systems to select inappropriate treatments for users, implement the inappropriate treatments, and/or identify that the treatments are inappropriate.

As indicated above, FIGS. 1A-1F are provided as an example. Other examples may differ from what is described with regard to FIGS. 1A-1F. The number and arrangement of devices shown in FIGS. 1A-1F are provided as an example. In practice, there may be additional devices, fewer devices, different devices, or differently arranged devices than those shown in FIGS. 1A-1F. Furthermore, two or more devices shown in FIGS. 1A-1F may be implemented within a single device, or a single device shown in FIGS. 1A-1F may be implemented as multiple, distributed devices. Additionally, or alternatively, a set of devices (e.g., one or more devices) shown in FIGS. 1A-1F may perform one or more functions described as being performed by another set of devices shown in FIGS. 1A-1F.

Figure 2:
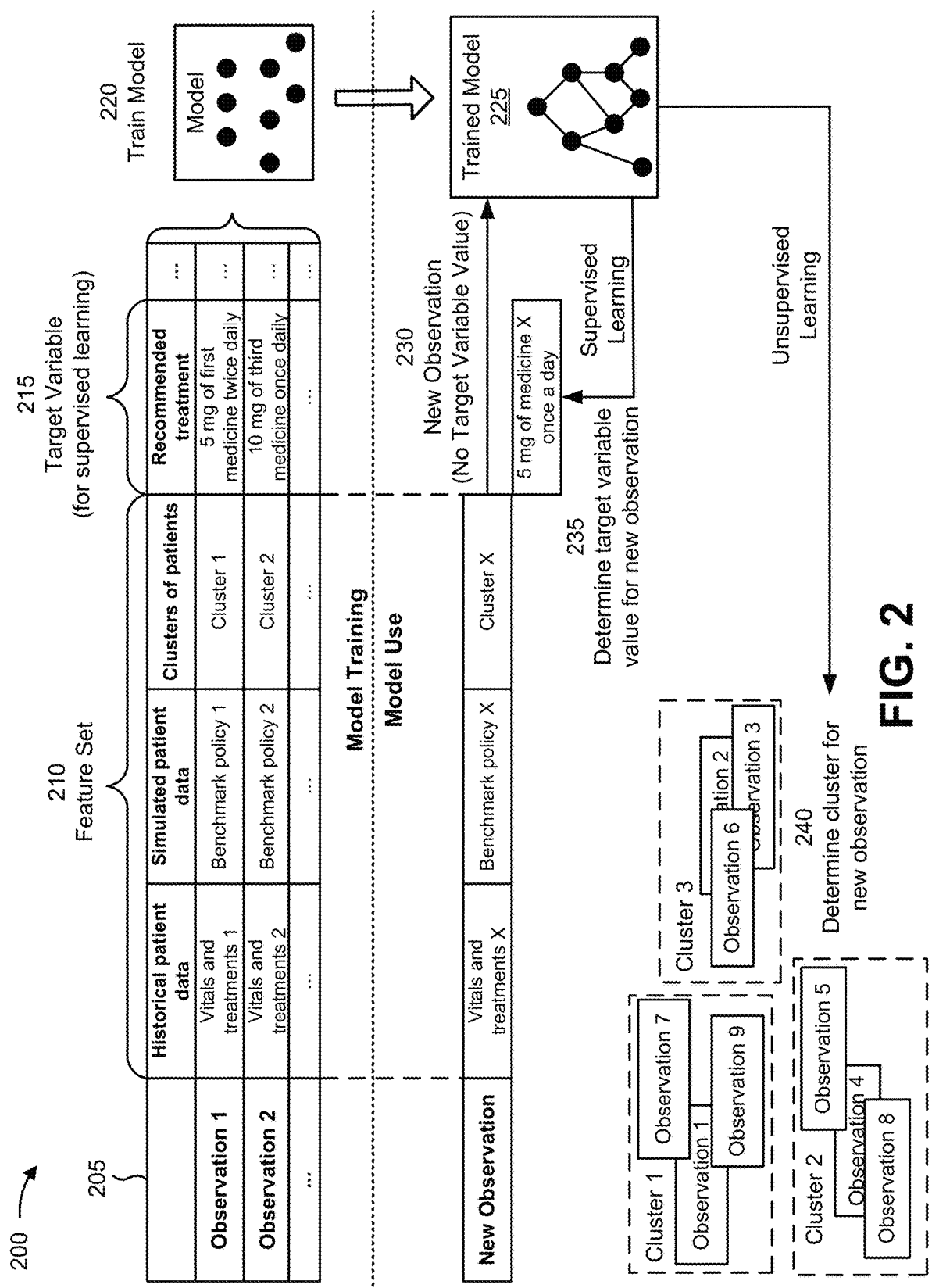
FIG. 2 is a diagram illustrating an example of training and using a machine learning model in connection with recommending and adapting treatments for users.

FIG. 2 is a diagram illustrating an example 200 of training and using a machine learning model in connection with recommending and adapting treatments for users. The machine learning model training and usage described herein may be performed using a machine learning system. The machine learning system may include or may be included in a computing device, a server, a cloud computing environment, and/or the like, such as the treatment system described in more detail elsewhere herein.

As shown by reference number 205, a machine learning model may be trained using a set of observations. The set of observations may be obtained from historical data, such as data gathered during one or more processes described herein. In some implementations, the machine learning system may receive the set of observations (e.g., as input) from the treatment system, as described elsewhere herein.

As shown by reference number 210, the set of observations includes a feature set. The feature set may include a set of variables, and a variable may be referred to as a feature. A specific observation may include a set of variable values (or feature values) corresponding to the set of variables. In some implementations, the machine learning system may determine variables for a set of observations and/or variable values for a specific observation based on input received from the treatment system. For example, the machine learning system may identify a feature set (e.g., one or more features and/or feature values) by extracting the feature set from structured data, by performing natural language processing to extract the feature set from unstructured data, by receiving input from an operator, and/or the like.

As an example, a feature set for a set of observations may include a first feature of historical user data, a second feature of simulated user data, a third feature of clusters of users, and so on. As shown, for a first observation, the first feature may have a value of vitals and treatments 1, the second feature may have a value of benchmark policy 1, the third feature may have a value of cluster 1, and so on. These features and feature values are provided as examples, and may differ in other examples.

As shown by reference number 215, the set of observations may be associated with a target variable. The target variable may represent a variable having a numeric value, may represent a variable having a numeric value that falls within a range of values or has some discrete possible values, may represent a variable that is selectable from one of multiple options (e.g., one of multiple classes, classifications, labels, and/or the like), may represent a variable having a Boolean value, and/or the like. A target variable may be associated with a target variable value, and a target variable value may be specific to an observation. In example 200, the target variable is a recommended treatment, which has a value of "5 milligrams (mg) of a first medicine twice daily" for the first observation and a value of "10 mg of a third medicine once daily" for the second observation.

The target variable may represent a value that a machine learning model is being trained to predict, and the feature set may represent the variables that are input to a trained machine learning model to predict a value for the target variable. The set of observations may include target variable values so that the machine learning model can be trained to recognize patterns in the feature set that lead to a target variable value. A machine learning model that is trained to predict a target variable value may be referred to as a supervised learning model.

In some implementations, the machine learning model may be trained on a set of observations that do not include a target variable. This may be referred to as an unsupervised learning model. In this case, the machine learning model may learn patterns from the set of observations without labeling or supervision, and may provide output that indicates such patterns, such as by using clustering and/or association to identify related groups of items within the set of observations.

As shown by reference number 220, the machine learning system may train a machine learning model using the set of observations and using one or more machine learning algorithms, such as a regression algorithm, a decision tree algorithm, a neural network algorithm, a k-nearest neighbor algorithm, a support vector machine algorithm, and/or the like. After training, the machine learning system may store the machine learning model as a trained machine learning model 225 to be used to analyze new observations.

As shown by reference number 230, the machine learning system may apply the trained machine learning model 225 to a new observation, such as by receiving a new observation and inputting the new observation to the trained machine learning model 225. As shown, the new observation may include a first feature of vitals and treatments X, a second feature of benchmark policy X, a third feature of cluster X, and so on, as an example. The machine learning system may apply the trained machine learning model 225 to the new observation to generate an output (e.g., a result). The type of output may depend on the type of machine learning model and/or the type of machine learning task being performed. For example, the output may include a predicted value of a target variable, such as when supervised learning is employed. Additionally, or alternatively, the output may include information that identifies a cluster to which the new observation belongs, information that indicates a degree of similarity between the new observation and one or more other observations, and/or the like, such as when unsupervised learning is employed.

As an example, the trained machine learning model 225 may predict a value of "5 mg of medicine X once a day" for the target variable of issue data for the new observation, as shown by reference number 235. Based on this prediction, the machine learning system may provide a first recommendation, may provide output for determination of a first recommendation, may perform a first automated action, may cause a first automated action to be performed (e.g., by instructing another device to perform the automated action), and/or the like.

In some implementations, the trained machine learning model 225 may classify (e.g., cluster) the new observation in a cluster, as shown by reference number 240. The observations within a cluster may have a threshold degree of similarity. As an example, if the machine learning system classifies the new observation in a first cluster (e.g., a historical user data cluster), then the machine learning system may provide a first recommendation. Additionally, or alternatively, the machine learning system may perform a first automated action and/or may cause a first automated action to be performed (e.g., by instructing another device to perform the automated action) based on classifying the new observation in the first cluster.

As another example, if the machine learning system were to classify the new observation in a second cluster (e.g., a simulated user data cluster), then the machine learning system may provide a second (e.g., different) recommendation and/or may perform or cause performance of a second (e.g., different) automated action.

In some implementations, the recommendation and/or the automated action associated with the new observation may be based on a target variable value having a particular label (e.g., classification, categorization, and/or the like), may be based on whether a target variable value satisfies one or more thresholds (e.g., whether the target variable value is greater than a threshold, is less than a threshold, is equal to a threshold, falls within a range of threshold values, and/or the like), may be based on a cluster in which the new observation is classified, and/or the like.

In this way, the machine learning system may apply a rigorous and automated process to recommend and adapt treatments for users. The machine learning system enables recognition and/or identification of tens, hundreds, thousands, or millions of features and/or feature values for tens, hundreds, thousands, or millions of observations, thereby increasing accuracy and consistency and reducing delay associated with recommending and adapting treatments for users relative to requiring computing resources to be allocated for tens, hundreds, or thousands of operators to manually recommend and adapt treatments for users.

As indicated above, FIG. 2 is provided as an example. Other examples may differ from what is described in connection with FIG. 2.

Figure 3:
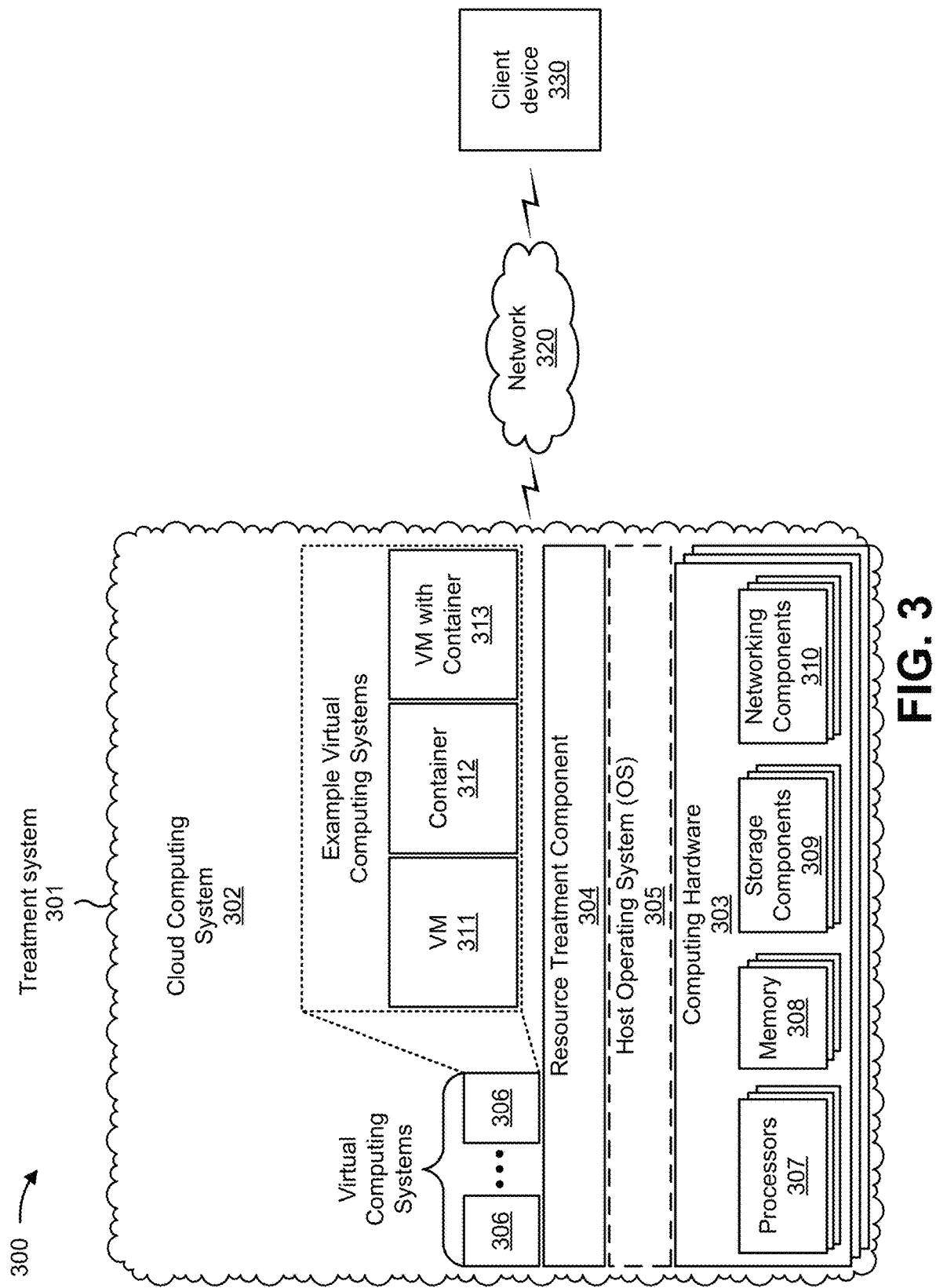
FIG. 3 is a diagram of an example environment in which systems and/or methods described herein may be implemented.

FIG. 3 is a diagram of an example environment 300 in which systems and/or methods described herein may be implemented. As shown in FIG. 3, environment 300 may include a treatment system 301, which may include one or more elements of and/or may execute within a cloud computing system 302. The cloud computing system 302 may include one or more elements 303-313, as described in more detail below. As further shown in FIG. 3, environment 300 may include a network 320 and/or a client device 330. Devices and/or elements of environment 300 may interconnect via wired connections and/or wireless connections.

The cloud computing system 302 includes computing hardware 303, a resource management component 304, a host operating system (OS) 305, and/or one or more virtual computing systems 306. The resource management component 304 may perform virtualization (e.g., abstraction) of computing hardware 303 to create the one or more virtual computing systems 306. Using virtualization, the resource management component 304 enables a single computing device (e.g., a computer, a server, and/or the like) to operate like multiple computing devices, such as by creating multiple isolated virtual computing systems 306 from computing hardware 303 of the single computing device. In this way, computing hardware 303 can operate more efficiently, with lower power consumption, higher reliability, higher availability, higher utilization, greater flexibility, and lower cost than using separate computing devices.

Computing hardware 303 includes hardware and corresponding resources from one or more computing devices. For example, computing hardware 303 may include hardware from a single computing device (e.g., a single server) or from multiple computing devices (e.g., multiple servers), such as multiple computing devices in one or more data centers. As shown, computing hardware 303 may include one or more processors 307, one or more memories 308, one or more storage components 309, and/or one or more networking components 310. Examples of a processor, a memory, a storage component, and a networking component (e.g., a communication component) are described elsewhere herein.

The resource management component 304 includes a virtualization application (e.g., executing on hardware, such as computing hardware 303) capable of virtualizing computing hardware 303 to start, stop, and/or manage one or more virtual computing systems 306. For example, the resource management component 304 may include a hypervisor (e.g., a bare-metal or Type 1 hypervisor, a hosted or Type 2 hypervisor, and/or the like) or a virtual machine monitor, such as when the virtual computing systems 306 are virtual machines 311. Additionally, or alternatively, the resource management component 304 may include a container manager, such as when the virtual computing systems 306 are containers 312. In some implementations, the resource management component 304 executes within and/or in coordination with a host operating system 305.

A virtual computing system 306 includes a virtual environment that enables cloud-based execution of operations and/or processes described herein using computing hardware 303. As shown, a virtual computing system 306 may include a virtual machine 311, a container 312, a hybrid environment 313 that includes a virtual machine and a container, and/or the like. A virtual computing system 306 may execute one or more applications using a file system that includes binary files, software libraries, and/or other resources required to execute applications on a guest operating system (e.g., within the virtual computing system 306) or the host operating system 305.

Although the treatment system 301 may include one or more elements 303-313 of the cloud computing system 302, may execute within the cloud computing system 302, and/or may be hosted within the cloud computing system 302, in some implementations, the treatment system 301 may not be cloud-based (e.g., may be implemented outside of a cloud computing system) or may be partially cloud-based. For example, the treatment system 301 may include one or more devices that are not part of the cloud computing system 302, such as device 400 of FIG. 4, which may include a stand-alone server or another type of computing device. The treatment system 301 may perform one or more operations and/or processes described in more detail elsewhere herein.

Network 320 includes one or more wired and/or wireless networks. For example, network 320 may include a cellular network, a public land mobile network (PLMN), a local area network (LAN), a wide area network (WAN), a private network, the Internet, and/or the like, and/or a combination of these or other types of networks. The network 320 enables communication among the devices of environment 300.

Client device 330 includes one or more devices capable of receiving, generating, storing, processing, and/or providing information, as described elsewhere herein. Client device 330 may include a communication device and/or a computing device. For example, client device 330 may include a wireless communication device, a user equipment (UE), a mobile phone (e.g., a smart phone or a cell phone, among other examples), a laptop computer, a tablet computer, a handheld computer, a desktop computer, a gaming device, a wearable communication device (e.g., a smart wristwatch or a pair of smart eyeglasses, among other examples), an Internet of Things (IoT) device, or a similar type of device. Client device 330 may communicate with one or more other devices of environment 300, as described elsewhere herein.

The number and arrangement of devices and networks shown in FIG. 3 are provided as an example. In practice, there may be additional devices and/or networks, fewer devices and/or networks, different devices and/or networks, or differently arranged devices and/or networks than those shown in FIG. 3. Furthermore, two or more devices shown in FIG. 3 may be implemented within a single device, or a single device shown in FIG. 3 may be implemented as multiple, distributed devices. Additionally, or alternatively, a set of devices (e.g., one or more devices) of environment 300 may perform one or more functions described as being performed by another set of devices of environment 300.

Figure 4:
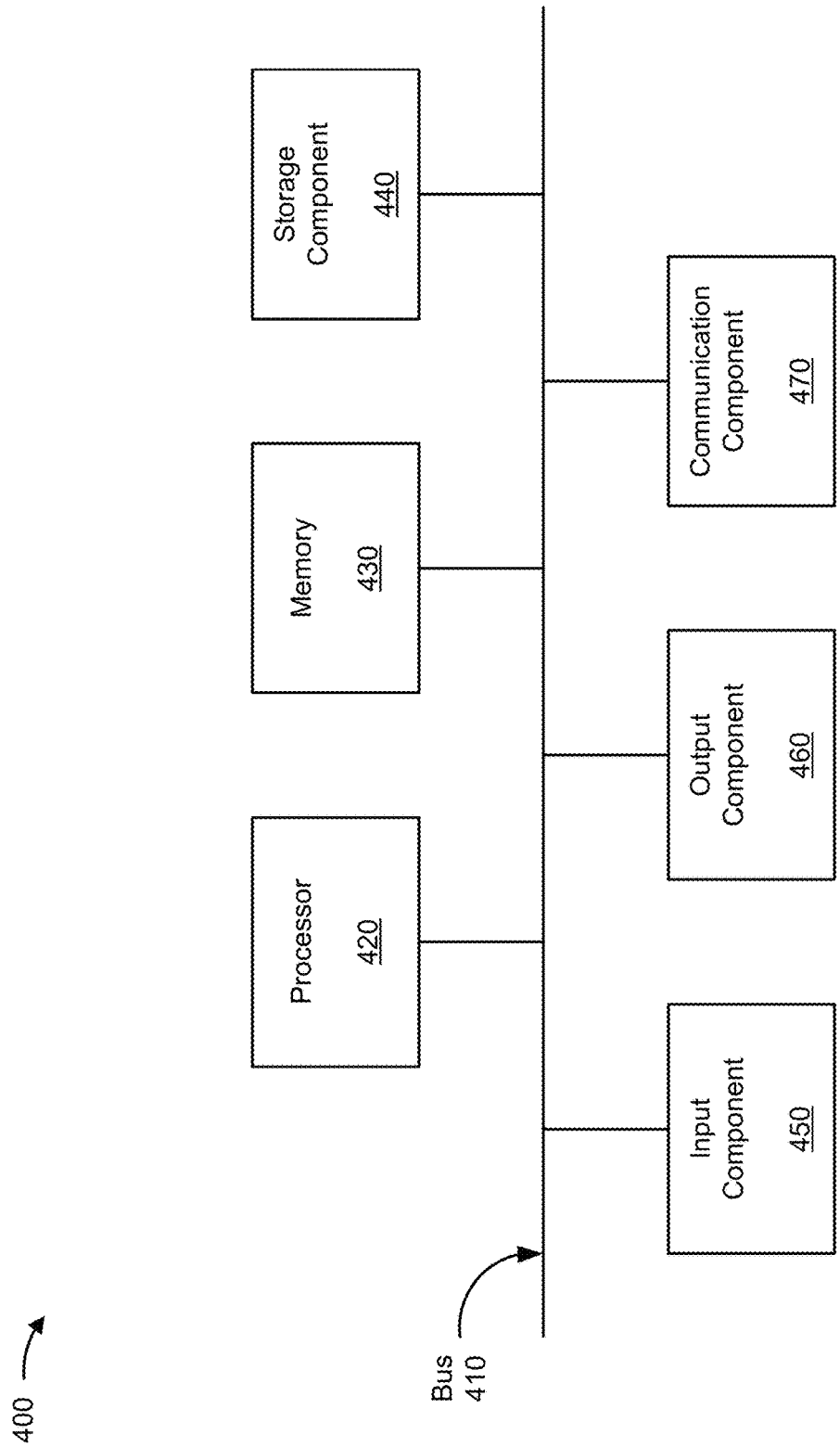
FIG. 4 is a diagram of example components of one or more devices of FIG. 3.

FIG. 4 is a diagram of example components of a device 400, which may correspond to treatment system 301 and/or client device 330. In some implementations, treatment system 301 and/or client device 330 may include one or more devices 400 and/or one or more components of device 400. As shown in FIG. 4, device 400 may include a bus 410, a processor 420, a memory 430, a storage component 440, an input component 450, an output component 460, and a communication component 470.

Bus 410 includes a component that enables wired and/or wireless communication among the components of device 400. Processor 420 includes a central processing unit, a graphics processing unit, a microprocessor, a controller, a microcontroller, a digital signal processor, a field-programmable gate array, an application-specific integrated circuit, and/or another type of processing component. Processor 420 is implemented in hardware, firmware, or a combination of hardware and software. In some implementations, processor 420 includes one or more processors capable of being programmed to perform a function. Memory 430 includes a random access memory, a read only memory, and/or another type of memory (e.g., a flash memory, a magnetic memory, and/or an optical memory).

Storage component 440 stores information and/or software related to the operation of device 400. For example, storage component 440 may include a hard disk drive, a magnetic disk drive, an optical disk drive, a solid state disk drive, a compact disc, a digital versatile disc, and/or another type of non-transitory computer-readable medium. Input component 450 enables device 400 to receive input, such as user input and/or sensed inputs. For example, input component 450 may include a touch screen, a keyboard, a keypad, a mouse, a button, a microphone, a switch, a sensor, a global positioning system component, an accelerometer, a gyroscope, an actuator, and/or the like. Output component 460 enables device 400 to provide output, such as via a display, a speaker, and/or one or more light-emitting diodes. Communication component 470 enables device 400 to communicate with other devices, such as via a wired connection and/or a wireless connection. For example, communication component 470 may include a receiver, a transmitter, a transceiver, a modem, a network interface card, an antenna, and/or the like.

Device 400 may perform one or more processes described herein. For example, a non-transitory computer-readable medium (e.g., memory 430 and/or storage component 440) may store a set of instructions (e.g., one or more instructions, code, software code, program code, and/or the like) for execution by processor 420. Processor 420 may execute the set of instructions to perform one or more processes described herein. In some implementations, execution of the set of instructions, by one or more processors 420, causes the one or more processors 420 and/or the device 400 to perform one or more processes described herein. In some implementations, hardwired circuitry may be used instead of or in combination with the instructions to perform one or more processes described herein. Thus, implementations described herein are not limited to any specific combination of hardware circuitry and software.

The number and arrangement of components shown in FIG. 4 are provided as an example. Device 400 may include additional components, fewer components, different components, or differently arranged components than those shown in FIG. 4. Additionally, or alternatively, a set of components (e.g., one or more components) of device 400 may perform one or more functions described as being performed by another set of components of device 400.

Figure 5:
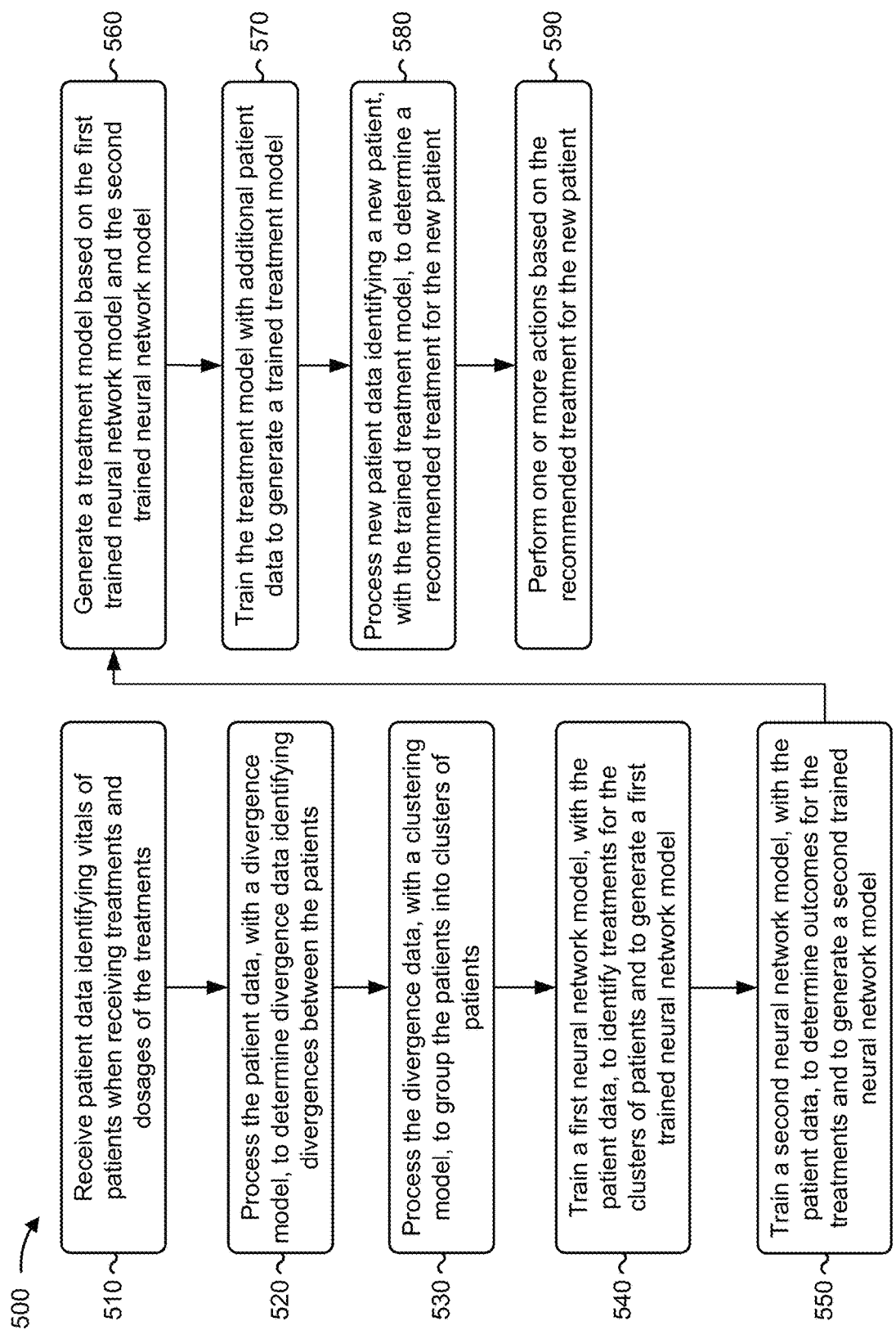
FIG. 5 is a flowchart of an example process for utilizing neural network models for recommending and adapting treatments for users.

FIG. 5 is a flowchart of an example process 500 for utilizing neural network models for recommending and adapting treatments for users. In some implementations, one or more process blocks of FIG. 5 may be performed by a device (e.g., treatment system 301). In some implementations, one or more process blocks of FIG. 5 may be performed by another device or a group of devices separate from or including the device, such as a client device (e.g., client device 330). Additionally, or alternatively, one or more process blocks of FIG. 5 may be performed by one or more components of device 400, such as processor 420, memory 430, storage component 440, input component 450, output component 460, and/or communication component 470.

As shown in FIG. 5, process 500 may include receiving user data identifying vitals of users when receiving treatments and dosages of the treatments (block 510). For example, the device may receive user data identifying vitals of users when receiving treatments and dosages of the treatments, as described above.

As further shown in FIG. 5, process 500 may include processing the user data, with a divergence model, to determine divergence data identifying divergences between the users (block 520). For example, the device may process the user data, with a divergence model, to determine divergence data identifying divergences between the users, as described above.

As further shown in FIG. 5, process 500 may include processing the divergence data, with a clustering model, to group the users into clusters of users (block 530). For example, the device may process the divergence data, with a clustering model, to group the users into clusters of users, as described above.

As further shown in FIG. 5, process 500 may include training a first neural network model, with the user data, to identify treatments for the clusters of users and to generate a trained first neural network model (block 540). For example, the device may train a first neural network model, with the user data, to identify treatments for the clusters of users and to generate a trained first neural network model, as described above.

As further shown in FIG. 5, process 500 may include training a second neural network model, with the user data, to determine outcomes for the treatments and to generate a trained second neural network model (block 550). For example, the device may train a second neural network model, with the user data, to determine outcomes for the treatments and to generate a trained second neural network model, as described above.

As further shown in FIG. 5, process 500 may include generating a treatment model based on the trained first neural network model and the trained second neural network model (block 560). For example, the device may generate a treatment model based on the trained first neural network model and the trained second neural network model, as described above.

As further shown in FIG. 5, process 500 may include training the treatment model with additional user data to generate a trained treatment model (block 570). For example, the device may train the treatment model with additional user data to generate a trained treatment model, as described above.

As further shown in FIG. 5, process 500 may include processing new user data identifying a new user, with the trained treatment model, to determine a recommended treatment for the new user (block 580). For example, the device may process new user data identifying a new user, with the trained treatment model, to determine a recommended treatment for the new user, as described above.

As further shown in FIG. 5, process 500 may include performing one or more actions based on the recommended treatment for the new user (block 590). For example, the device may perform one or more actions based on the recommended treatment for the new user, as described above.

Process 500 may include additional implementations, such as any single implementation or any combination of implementations described below and/or in connection with one or more other processes described elsewhere herein.

In a first implementation, receiving the user data includes receiving historical user data identifying historical vitals of the users when receiving the treatments and historical dosages of the treatments, and receiving simulated user data identifying simulated vitals of the users when receiving the treatments and simulated dosages of the treatments.

In a second implementation, alone or in combination with the first implementation, process 500 includes processing the new user data, with the divergence model, to determine new divergence data identifying a divergence of the new user, and processing the new divergence data, with the clustering model, to assign the new user to one of the clusters of users prior to processing the new user data with the trained treatment model.

In a third implementation, alone or in combination with one or more of the first and second implementations, processing the user data, with the divergence model, to determine the divergence data identifying the divergences between the users includes calculating pairwise Jensen-Shannon divergences between the users, and generating a distance matrix based on the pairwise Jensen-Shannon divergences between the users, wherein the distance matrix corresponds to the divergence data.

In a fourth implementation, alone or in combination with one or more of the first through third implementations, processing the divergence data, with the clustering model, to group the users into the clusters of users includes applying a hierarchical clustering model to the divergence data to group the users into the clusters of users.

In a fifth implementation, alone or in combination with one or more of the first through fourth implementations, training the first neural network model, with the user data, to identify the treatments for the clusters of users and to generate the trained first neural network model includes calculating variances associated with the treatments for the clusters of users, and generating the trained first neural network model when the variances satisfy a threshold variance.

In a sixth implementation, alone or in combination with one or more of the first through fifth implementations, training the second neural network model, with the user data, to determine the outcomes for the treatments and to generate the trained second neural network model includes calculating variances associated with the outcomes for the treatments, and generating the trained second neural network model when the variances satisfy a threshold variance.

In a seventh implementation, alone or in combination with one or more of the first through sixth implementations, process 500 includes causing the recommended treatment to be implemented for the new user; receiving outcome information identifying outcomes associated with implementing the recommended treatment for the new user; and adapting the trained treatment model for the new user based on the outcome information.

In an eighth implementation, alone or in combination with one or more of the first through seventh implementations, process 500 includes determining an updated recommended treatment for the new user based on adapting the trained treatment model for the new user, and causing the updated recommended treatment to be implemented for the new user.

In a ninth implementation, alone or in combination with one or more of the first through eighth implementations, performing the one or more actions based on the recommended treatment includes causing the new user to receive the recommended treatment; receiving feedback associated with the new user receiving the recommended treatment; and updating the trained treatment model based on the feedback.

In a tenth implementation, alone or in combination with one or more of the first through ninth implementations, performing the one or more actions based on the recommended treatment includes defining a range of treatments for the new user based on the recommended treatment and based on a risk threshold, and causing the new user to receive the range of treatments.

In an eleventh implementation, alone or in combination with one or more of the first through tenth implementations, performing the one or more actions based on the recommended treatment includes causing the new user to receive the recommended treatment; monitoring vitals of the new user when receiving the recommended treatment; and updating the recommended treatment based on the vitals.

In a twelfth implementation, alone or in combination with one or more of the first through eleventh implementations, performing the one or more actions based on the recommended treatment includes retraining one or more of the divergence model, the clustering model, the first neural network model, or the second neural network model based on the recommended treatment.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

The foregoing disclosure provides illustration and description, but is not intended to be exhaustive or to limit the implementations to the precise form disclosed. Modifications may be made in light of the above disclosure or may be acquired from practice of the implementations.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

As used herein, satisfying a threshold may, depending on the context, refer to a value being greater than the threshold, greater than or equal to the threshold, less than the threshold, less than or equal to the threshold, equal to the threshold, and/or the like, depending on the context.

Although particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
receiving, by a device, user data identifying vitals of users when receiving treatments and dosages of the treatments;
processing, by the device, the divergence data, with a clustering model, to group the users into clusters of users, wherein the clustering model includes a hierarchical clustering model and comprises applying the hierarchical clustering model to the divergence data to group the users into the clusters of users;
training, by the device, a first neural network model, with the user data, to identify treatments for the clusters of users and to generate a trained first neural network model, wherein the training of the first neural network model includes:
receiving, by the device, a set of observations;
determining, by the device, a target variable for the set of observations; and
training, by the device, the first neural network model using the target variable;
training, by the device, a second neural network model, with the user data, to determine simulated outcomes for the treatments and to generate a trained second neural network model, wherein the training of the second neural network model includes:
obtaining, by the device, additional user data;
determining, by the device, the simulation of outcomes based on the additional user data; and
causing, by the device, the second neural network model to train, based on the simulated outcome;
generating, by the device, a treatment model based on the trained first neural network model and the trained second neural network model;
training, by the device, the treatment model with the additional user data to generate a trained treatment model;
processing, by the device, new user data identifying a new user, with the trained treatment model, to determine a recommended treatment for the new user; and
performing, by the device, one or more actions based on the recommended treatment for the new user.

2. The method of claim 1, wherein receiving the user data comprises:
receiving historical user data identifying historical vitals of the users when receiving the treatments and historical dosages of the treatments; and
receiving simulated user data identifying simulated vitals of the users when receiving the treatments and simulated dosages of the treatments.

3. The method of claim 1, further comprising:
processing the new user data, with the divergence model, to determine new divergence data identifying a divergence between the clusters of users and the new user; and
processing the new divergence data, with the clustering model, to assign the new user to one of the clusters of users prior to processing the new user data with the trained treatment model.

4. The method of claim 1, wherein processing the user data, with the divergence model, to determine the divergence data identifying the divergences between the users comprises:
calculating pairwise Jensen-Shannon divergences between the users; and
generating a distance matrix based on the pairwise Jensen-Shannon divergences between the users, wherein the distance matrix corresponds to the divergence data.

5. The method of claim 1, wherein training the first neural network model, with the user data, to identify the treatments for the clusters of users and to generate the trained first neural network model comprises:
calculating variances associated with the treatments for the clusters of users; and
generating the trained first neural network model when the variances satisfy a threshold variance.

6. The method of claim 1, wherein training the second neural network model, with the user data, to determine the outcomes for the treatments and to generate the trained second neural network model comprises:
calculating variances associated with the outcomes for the treatments; and
generating the trained second neural network model when the variances satisfy a threshold variance.

7. A device, comprising:
one or more memories; and
one or more processors, communicatively coupled to the one or more memories, configured to:
receive user data identifying vitals of users when receiving treatments and dosages of the treatments, wherein the user data includes one of:
historical user data identifying historical vitals of the users when receiving the treatments and historical dosages of the treatments, or
simulated user data identifying simulated vitals of the users when receiving the treatments and simulated dosages of the treatments;
process the user data, with a divergence model, to determine divergence data identifying divergences between the users, wherein the divergence model uses a kernel density estimation (KDE) and a Jensen-Shannon method to determine divergences between the users;
process the divergence data, with a clustering model, to group the users into clusters of users, wherein the clustering model includes a hierarchical clustering model and comprises applying the hierarchical clustering model to the divergence data to group the users into the clusters of users;
train a first neural network model, with the user data, to identify treatments for the clusters of users and to generate a trained first neural network model, wherein the training of the first neural network model includes:
receiving, by the device, a set of observations;
determining, by the device, a target variable for the set of observations; and
training, by the device, the first neural network model using the target variable;
train a second neural network model, with the user data, to determine simulated outcomes for the treatments and to generate a trained second neural network model, wherein the training of the second neural network includes:
obtaining, by the device, additional user data;
determining, by the device, the simulation of outcomes based on the additional user data; and
causing, by the device, the second neural network model to train, based on the simulated outcome;
generate a treatment model based on the trained first neural network model and the trained second neural network model;
train the treatment model with the additional user data to generate a trained treatment model;
process new user data identifying a new user, with the trained treatment model, to determine a recommended treatment for the new user; and
perform one or more actions based on the recommended treatment for the new user.

8. The device of claim 7, wherein the one or more processors are further configured to:
cause the recommended treatment to be implemented for the new user;
receive outcome information identifying outcomes associated with implementing the recommended treatment for the new user; and
adapt the trained treatment model for the new user based on the outcome information.

9. The device of claim 8, wherein the one or more processors are further configured to:
determine an updated recommended treatment for the new user based on adapting the trained treatment model for the new user; and
cause the updated recommended treatment to be implemented for the new user.

10. The device of claim 7, wherein the one or more processors, when performing the one or more actions based on the recommended treatment, are configured to:
cause the new user to receive the recommended treatment;
receive feedback associated with the new user receiving the recommended treatment; and
update the trained treatment model based on the feedback.

11. The device of claim 7, wherein the one or more processors, when performing the one or more actions based on the recommended treatment, are configured to:
define a range of treatments for the new user based on the recommended treatment and based on a risk threshold; and
cause the new user to receive the range of treatments.

12. The device of claim 7, wherein the one or more processors, when performing the one or more actions based on the recommended treatment, are configured to:
cause the new user to receive the recommended treatment;
monitor vitals of the new user when receiving the recommended treatment; and
update the recommended treatment based on the vitals.

13. The device of claim 7, wherein the one or more processors, when performing the one or more actions based on the recommended treatment, are configured to:
retrain one or more of the divergence model, the clustering model, the first neural network model, or the second neural network model based on the recommended treatment,
wherein the first neural network model and the second neural network model implement a reinforcement learning model.

14. A non-transitory computer-readable medium storing a set of instructions, the set of instructions comprising:
one or more instructions that, when executed by one or more processors of a device, cause the device to:
receive user data identifying vitals of users when receiving treatments and dosages of the treatments;
process the user data, with a divergence model, to determine divergence data identifying divergences between the users, wherein the divergence model uses a kernel density estimation (KDE) and a Jensen-Shannon method to determine divergences between the users;
process the divergence data, with a clustering model, to group the users into clusters of users, wherein the clustering model includes a hierarchical clustering model and comprises applying the hierarchical clustering model to the divergence data to group the users into the clusters of users;
train a first neural network model, with the user data, to identify treatments for the clusters of users and to generate a trained first neural network model, wherein the training of the first neural network model includes:
receiving, by the device, a set of observations;
determining, by the device, a target variable for the set of observations; and
training, by the device, the first neural network model using the target variable;

train a second neural network model, with the user data, to determine simulated outcomes for the treatments and to generate a trained second neural network model, wherein the training of the second neural network model includes:
  obtaining, by the device, additional user data;
  determining, by the device, the simulation of outcomes based on the additional user data; and
  causing, by the device, the second neural network model to train, based on the simulated outcome;
generate a treatment model based on the trained first neural network model and the trained second neural network model;
train the treatment model with the additional user data to generate a trained treatment model;
process new user data identifying a new user, with the divergence model, to determine new divergence data identifying a divergence between the clusters of users and the new user;
process the new divergence data, with the clustering model, to assign the new user to one of the clusters of users;
process the new user data, with the trained treatment model, to determine a recommended treatment for the new user based on the one of the clusters of users assigned to the new user; and
perform one or more actions based on the recommended treatment for the new user.

15. The non-transitory computer-readable medium of claim 14, wherein the one or more instructions, that cause the device to process the user data, with the divergence model, to determine the divergence data identifying the divergences between the users, cause the device to:
  calculate pairwise Jensen-Shannon divergences between the users; and
  generate a distance matrix based on the pairwise Jensen-Shannon divergences between the users,
    wherein the distance matrix corresponds to the divergence data.

16. The non-transitory computer-readable medium of claim 14, wherein the one or more instructions, that cause the device to train the first neural network model, with the user data, to identify the treatments for the clusters of users and to generate the trained first neural network model, cause the device to:
  calculate variances associated with the treatments for the clusters of users; and
  generate the trained first neural network model when the variances satisfy a threshold variance.

17. The non-transitory computer-readable medium of claim 14, wherein the one or more instructions, that cause the device to train the second neural network model, with the user data, to determine the outcomes for the treatments and to generate the trained second neural network model, cause the device to:
  calculate variances associated with the outcomes for the treatments; and
  generate the trained second neural network model when the variances satisfy a threshold variance.

18. The non-transitory computer-readable medium of claim 14, wherein the one or more instructions further cause the device to:
  cause the recommended treatment to be implemented for the new user;
  receive outcome information identifying outcomes associated with implementing the recommended treatment for the new user;
  adapt the trained treatment model for the new user based on the outcome information;
  determine an updated recommended treatment for the new user based on adapting the trained treatment model for the new user; and
  cause the updated recommended treatment to be implemented for the new user.

* * * * *